US008481478B2

(12) United States Patent
Hellerstein

(10) Patent No.: US 8,481,478 B2
(45) Date of Patent: *Jul. 9, 2013

(54) METHOD FOR AUTOMATED, LARGE-SCALE MEASUREMENT OF THE MOLECULAR FLUX RATES OF THE PROTEOME OR THE ORGANEOME USING MASS SPECTROMETRY

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,183

(22) Filed: Mar. 1, 2012

(65) Prior Publication Data

US 2012/0190560 A1    Jul. 26, 2012

Related U.S. Application Data

(63) Continuation of application No. 12/534,807, filed on Aug. 3, 2009, now Pat. No. 8,129,335, which is a continuation of application No. 10/523,250, filed as application No. PCT/US03/23340 on Jul. 25, 2003, now abandoned.

(60) Provisional application No. 60/399,950, filed on Jul. 30, 2002.

(51) Int. Cl.
*A61K 38/00* (2006.01)

(52) U.S. Cl.
USPC .......................................................... 514/1.1

(58) Field of Classification Search
None
See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zolotarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami |
| 6,329,208 B1 | 12/2001 | Jones et al. |
| 6,355,416 B1 | 3/2002 | Abramson |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 * | 12/2003 | Aebersold et al. ............ 436/173 |
| 6,680,203 B2 | 1/2004 | Dasseux et al. |
| 6,764,817 B1 * | 7/2004 | Schneider ........................ 435/4 |
| 6,783,751 B2 | 8/2004 | Heumann |
| 6,808,875 B2 | 10/2004 | Hellerstein |
| 6,835,927 B2 | 12/2004 | Becker et al. |

(Continued)

FOREIGN PATENT DOCUMENTS

| | | |
|---|---|---|
| CA | 2494715 A1 | 2/2004 |
| EP | 0826377 B1 | 11/2002 |

(Continued)

OTHER PUBLICATIONS

Hinkson et al., The dynamic state of protein turnover: Its about time, Trends in Cell Biology, May 2011, vol. 21, No. 5.*
Previs et al., A critical evaluation of mass isotopomer distribution analysis of gluconeogenesis in vivo, American Journal of Physiology-Endocrinology and Metabolism, vol. 277 No. 1 (Jul. 1999), E154-E160.*
Nordhoff et al., Mass Spectroscopy of Nucleic Acids, Mass spectrometry Reviews, vol. 15, Issue 2, (Dec. 21, 1998), pp. 67-138.*
Szymanski et al., Beyond the proteome: non-coding regulatory RNAs, Genome Biology (Apr. 2002), vol. 3 issue 5.*
Hellerstein et. al., Measurement of human plasma proteome dynamics with 2H2O and liquid chromatography tandem mass spectrometry, Analytical Biochemistry 420 (2012) 73-83.*

(Continued)

*Primary Examiner* — Cecilia J Tsang
*Assistant Examiner* — Randall L Beane
(74) *Attorney, Agent, or Firm* — Morrison & Foerster LLP

(57) ABSTRACT

Disclosed here is a method for measuring the kinetics (i.e., the molecular flux rates—synthesis and breakdown or removal rates) of a plurality of proteins or organic metabolites in living systems. The methods may be accomplished in a high-throughput, large-scale automated manner, by using existing mass spectrometric profiling techniques and art well known in the fields of static proteomics and static organeomics, without the need for additional biochemical preparative steps or analytic/instrumental devices.

18 Claims, 6 Drawing Sheets

U.S. PATENT DOCUMENTS

| | | | |
|---|---|---|---|
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 | 2/2006 | Hellerstein |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 | 12/2007 | Hellerstein |
| 7,357,913 B2 | 4/2008 | Hellerstein |
| 7,410,633 B2 | 8/2008 | Hellerstein |
| 7,449,171 B2 | 11/2008 | Hellerstein |
| 7,504,233 B2 | 3/2009 | Hellerstein |
| 7,910,323 B2 | 3/2011 | Hellerstein |
| 8,005,623 B2 | 8/2011 | Hellerstein |
| 8,021,644 B2 | 9/2011 | Hellerstein |
| 2003/0068634 A1 | 4/2003 | Hellerstein |
| 2003/0119069 A1 | 6/2003 | Schneider et al. |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza, Jr. et al. |
| 2005/0014181 A1 | 1/2005 | Galis et al. |
| 2005/0092910 A1 | 5/2005 | Geromanos et al. |
| 2005/0118724 A1 | 6/2005 | Bateman et al. |
| 2005/0153346 A1 | 7/2005 | Schneider |
| 2005/0175982 A1 | 8/2005 | Iwatani et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0020440 A1 | 1/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0251576 A1 | 11/2006 | Hellerstein |
| 2006/0280682 A1 | 12/2006 | Hellerstein |
| 2007/0248540 A1 | 10/2007 | Hellerstein |
| 2008/0003179 A1 | 1/2008 | Hellerstein |
| 2009/0041661 A1 | 2/2009 | Hellerstein |

FOREIGN PATENT DOCUMENTS

| | | | |
|---|---|---|---|
| JP | 2001-211782 A | 8/2001 |
| JP | 2003-079270 A | 3/2003 |
| SU | 968036 A1 | 10/1982 |
| WO | 90/11371 A1 | 10/1990 |
| WO | 93/20800 A1 | 10/1993 |
| WO | 93/25705 A1 | 12/1993 |
| WO | 95/13096 A1 | 5/1995 |
| WO | 98/51820 A1 | 11/1998 |
| WO | 00/12535 A2 | 3/2000 |
| WO | 00/13025 A1 | 3/2000 |
| WO | 00/63683 A1 | 10/2000 |
| WO | 01/80715 A2 | 11/2001 |
| WO | 01/84143 A1 | 11/2001 |
| WO | 03/061479 A1 | 7/2003 |
| WO | 03/068919 A2 | 8/2003 |
| WO | 03/087314 A2 | 10/2003 |
| WO | 2004/003493 A2 | 1/2004 |
| WO | 2004/011426 A2 | 2/2004 |
| WO | 2004/016156 A2 | 2/2004 |
| WO | 2004/021863 A2 | 3/2004 |
| WO | 2004/024941 A2 | 3/2004 |
| WO | 2004/025270 A2 | 3/2004 |
| WO | 2004/042360 A2 | 5/2004 |
| WO | 2004/016156 A3 | 6/2004 |
| WO | 2005/009597 A2 | 2/2005 |
| WO | 2005/015155 A2 | 2/2005 |
| WO | 2005/033652 A2 | 4/2005 |
| WO | 2006/050130 A2 | 5/2006 |
| WO | 2006/081521 A2 | 8/2006 |
| WO | 2006/107814 A2 | 10/2006 |

OTHER PUBLICATIONS

Papageorgopoulos et al. (Measuring Protein Synthesis by Mass Isotopomer Distribution Analysis (MIDA), Analytical Biochemistry (1999), vol. 267, pp. 1-16.*

Chobanian et al., "Body Cholesterol Metabolism in Man. II. Measurement of the Body Cholesterol Miscible pool and Turnover Rate", Journal of Clinical Investigation, vol. 41, No. 9, 1962, pp. 1738-1744.

Duane, William C., "Measurement of Bile Acid Synthesis by Three Different Methods in Hypertriglyceridemic and Control Subjects", Journal of Lipid Research, vol. 38, 1997, pp. 183-188.

Ferezou et al., "Origins of Neutral Sterols in Human Feces Studied by Stable Isotope Labeling Deuterium and Carbon-13 Existence of an External Secretion of Cholesterol", Digestion, vol. 21, No. 5, 1981, pp. 232-243.

Landau et al., "Use of 2H2O for Estimating Rates of Gluconeogenesis", Journal of Clinical Investigation, vol. 95, Jan. 1995, pp. 172-178.

Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.

Rittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.

Rittler et al., "Effect of Tumor Removal on Mucosal Protein Synthesis in Patients with Colorectal Cancer", American Journal of Physiology-Endocrinology and Metabolism, vol. 284, 2003, pp. E1018-E1021.

Roberts, "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.

Robin et al., "Mitochondria DNA Molecules and Virtual Number of Mitochondria per Cell in Mammalian Cells", Journal of Cellular Physiology, vol. 136, 1988, pp. 507-513.

Robosky, L. C., "In Vivo Toxicity Screening Programs Using Metabonomics", Combinatorial Chemistry & High Throughput Screening., vol. 5, 2002, pp. 651-662.

Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.

Roda et al., "Results with Six 'Kit' Radioimmunoassays for Primary Bile Acids in Human Serum Intercompared", Clin. Chem., vol. 26, No. 12, 1980, pp. 1677-1682.

Roederer, M. "T-Cell Dynamics of Immunodeficiency", Nature Medicine, vol. 1, No. 7, Jul. 1995, pp. 621-622.

Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.

Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.

Royale et al., "Techniques for Investigating Substrate Metabolism in Patients", Annals of the Royal College of Surgeons of England, vol. 63, 1981, pp. 415-419.

Santarelli et al., "Requirement of Hippocampal Neurogenesis for the Behavioral Effects of Antidepressants", Science, vol. 301, No. 5634, Aug. 8, 2003, pp. 805-809.

Sawada et al., "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver", Mutation Research, vol. 344, 1995, pp. 109-116.

Scalise, K., "Tracking T-Cells in AIDS Patients: A Safe Reliable Method of Measuring Human Cell Generation Rates", Berkeleyan, Feb. 11-17, 1998, 3 pages.

Scheibner et al., "Bile Acid Synthesis from Newly Synthesized Vs. Preformed Cholesterol Precursor Pools in the Rat", Hepatology, vol. 17, 1993, pp. 1095-1102.

Scheibner et al., "Complex Feedback Regulation of Bile Acid Synthesis in the Hamster: The Role of Newly Synthsized Cholesterol", Hepatology, vol. 30, 1999, pp. 230-237.

Schneiter et al., "Kinetics of Dexamethasone Induced Alterations of Glucose Metabolism in Healthy Humans", American Journal of Physiology, 1998, pp. E806-E813.

Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.

Schwarz et al., "Short-Term Alterations in Carbohydrate Energy Intake in Humans", J. Clin. Invest., vol. 96, 1995, pp. 2735-2743.

Australian Patent Office Search Report mailed Aug. 26, 2005, for Singapore patent application No. SG 200500571-5, filed Jul. 25, 2003, 5 pages.

Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.

Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.

Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.

Siler et al., "The Inhibition of Gluconeogenesis Following Alcohol in Humans", Am. J. Physiol., vol. 275, 1998, pp. E897-E907.

Siler et al., "VLDL-Triglyceride Production After Alcohol Ingestion, Studied Using [2-13C1] Glycerol", J. Lipid Res., vol. 39, 1998, pp. 2319-2328.

Smith et al., "The Phosphogluconate Odixative Pathway", in Principles of Biochemistry, 7th edition, McGraw-Hill Book Company, 1983, pp. 417-423.

Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.

Sprent et al., "CD4+ Cell Turnover", Nature, vol. 375, 1995, 194 pages.

Stingl, et al., "Purification and Unique Properties of Mammary Epithelial Stem Cells", Nature, vol. 439, Feb. 2006, pp. 993-997.

Stingl et al., "Characterization of Bipotent Mammary Epithelial Progenitor Cells in Normal Adult Human Breast Tissue", Breast Can Res and Treatment, vol. 67, 2001, pp. 93-109.

Sunter et al., "Cell Population Kinetics in the Epithelium of the Colon of the Male Rat", Virchows Archiv. B Cell Path., vol. 26, 1978, pp. 275-287.

Teixeira et al., "Poor CD4 T Cell Restoration After Supression of HIV-1 Replication May Reflect Lower Thymic Function", AIDS, vol. 15, No. 14, 2001, pp. 1749-1756.

Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.

Traber et al., "Isolation of Intestinal Epithelial Cells for the Study of Differential Gene Expression Along the Crypt-Villus Axis", Am. J. Physiol., vol. 260, 1991, pp. G895-G903.

Trappe et al., "Effect of Ibuprofen and Acetaminophen on Postexercise Muscle Protein Synthesis", Am J Physiology Endocronol Metab, vol. 282, 2002, pp. E551-E556.

Turner, S. M., "Stable Isotopes, Mass Spectrometry, and Molecular Fluxes: Applications to Toxicology", Journal of Pharmacological and Toxicological Methods, vol. 53, 2006, pp. 75-85.

Turner et al., "Emerging Applications of Kinetic Biomarkers in Preclinical and Clinical Drug Development", Current Opinion in Drug Discovery & Development, vol. 8, No. 1, 2005, pp. 115-126.

Turner et al., "Measurement of Triglyceride (TG) Synthesis in Vivo 2H2O Incorporation into TG-Glycerol and Application of Mass Isotopomer Distribution Analysis (MIDA)", Experimental Biology, 2002 16 [Meeting Abstract 361.9], A400.

Van Hinsbergh et al., "Palmitate Oxidation by Rat Skeletal Muscle Mitochondria", Archives of Biochemistry and Biophysics, vol. 190, No. 2, 1978, pp. 762-771.

Van Loan et al., "Monitoring Changes in Fat-Free Mass in HIV-Positive Men with Hypotestosteronemia and AIDS Wasting Syndrome Treated with Gonadal Hormone Replacement Therapy", AIDS, vol. 13, 1999, pp. 241-248.

Veenstra et al., "Proteome Analysis Using Selective Incorporation of Isotopically Labeled Amino Acids", J. Am. Soc. Mass. Spectrom., vol. 11, 2000, pp. 78-82.

Veerkamp et al., "14CO2 Production is no Adequate Measure of [14C]Fatty Acid Oxidation", Biochemical Medicine and Metabolic Biology, vol. 35, 1986, pp. 248-259.

Véniant et al., "Defining the Atherogenicity of Large and Small Lipoproteins Containing Apolipoproteins B100", J. Clin. Invest., vol. 106, No. 12, 2000, pp. 1501-1510.

Wadke, "Fatty Acid Synthesis by Liver Perfused with Deuterated and Tritiated Water", Biochemistry, vol. 12, No. 14, 1973, pp. 2619-2624.

Wain-Hobson, S., "Virological Mayhem", Nature, vol. 373, 1995, 102 pages.

Waldeman et al., "A Comparison Between Bromodeoxyuridine and 3 H Thymidine Labeling in Human Breast Tumors", Modern Path., vol. 4, No. 6, 1991, pp. 718-722.

Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.

Waterlow, "Protein Turnover in the Whole Animal", Invest. Cell Pathol. vol. 3, 1980, pp. 107-119.

Wei et al., "Viral Dynamics in Human Immunodeficiency Virus Type 1 Infection", Nature, vol. 373, 1995, pp. 117-122.

McLean et al., "In Vivo Estimates of Division and Death Rates of Human T Lymphocytes", Proc. Natl. Acad. Sci USA, vol. 92, 1995, pp. 3707-3711.

Meier et al., "Rates of Protein Synthesis and Turnover in Fetal Life", Am J Physiol., vol. 240, No. 3, 1981, pp. E320-E324.

Mellors et al., "Prognosis in HIV-1 Infection Predicted by the Quantity of Virus in Plasma", Science, vol. 272, 1996, pp. 1167-1170.

Mellors et al., "Quantitation of HIV-1 RNA in Plasma Predicts Outcome after Seroconversion", Ann. Intern. Med., vol. 122, 1995, pp. 573-579.

Messmer et al., "In Vivo Measurements Document the Dynamic Cellular Kinetics of Chronic Lymphocytic Leukemia B Cells", J. Clin. Invest., vol. 115, Feb. 10, 2005, pp. 755-764.

Mewissen et al., "Comparative Incorporation of Tritium from Tritiated Water Versus Tritiated Thymidine, Uridine or Leucine", Curr. Top Rad. Res. Quart., vol. 12, 1977, pp. 225-254.

Michie et al., "Lifespan of Human Lymphocyte Subsets Defined by CD45 Isoforms,", Nature, vol. 360, 1992, pp. 264-265.

Mikkola et al., "Serum Cholesterol Efflux Potential is an Independent Predictor of Coronary Artery Atherosclerosis", Atherosclerosis, vol. 170, 2003, pp. 31-38.

Mindham et al., "Application of Simultaneous Spleen and Liver Perfusion to the Study of Reverse Cholesterol Transport", Biochemical Journal, vol. 302, 1994, pp. 207-213.

Misell et al., "A new in Vivo Stable Isotope Method for Measuring Mammary Epithelial Cell Proliferation", Faseb Journal Experimental Biology, vol. 14, No. 4, 2000, p. 550.

Mohri et al., "Increased Turnover of T Lymphocytes in HIV-1 Infection and its Reduction by Antiretroviral Therapy", J. Exp. Med., vol. 194, No. 9, 2001, pp. 1277-1287.

Morris et al., "Evidence that a Slowly Cycling Subpopulation of Adult Murine Epidermal Cells Retains Carcinogen", Cancer Research, vol. 46, 1997, pp. 3061-3066.

Morris et al., "Evidence that Cutaneous Carcinogen-Initiated Epithelial Cells from Mice are Quiescent Rather than Actively Cycling", Cancer Research, vol. 57, 1997, pp. 3436-3443.

Morsches, "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.

Mosier, D. E., "CD4.sup.+ Cell Turnover", Nature, vol. 375, 1995, pp. 193-194.

Murali-Krishna et al., "Counting Antigen-Specific CD8 T Cells: A Reevaluation of Bystander Activation during Viral Infection", Immunity, vol. 8, 1998, pp. 177-187.

Nagasaka et al., "Endogenous Glucose Production and Glucose Effectiveness in Type 2 Diabetic Subjects Derived From Stable-Labeled Minimal Modal Approach", Diabetes, vol. 48, May 1999, pp. 1054-1056.

Naik et al., "Pharmacological Activation of Liver X Receptors Promotes Reverse Cholesterol Transport In Vivo", Circulation, vol. 113, 2006, pp. 90-97.

Nanjee et al., "Intravenous apoA-I/lecithin Discs Increase Pre-Beta-HDL Concentration in Tissue Fluid and Stimulate Reverse Cholesterol Transport in Humans", Journal of Lipid Research, vol. 42, 2001, pp. 1586-1593.

Neese et al., "Advances in the Stable Isotope-Mass Spectrometric Measurement of DNA Synthesis and Cell Proliferation", Analytical Biochemistry, vol. 298, No. 2, 2001, pp. 189-195.

Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.

Neese et al., "Measurement of Endogenous Synthesis of Plasma Cholesterol in Rats and Humans Using MIDA", Am. J. Physiol., vol. 264, 1993, pp. E139-E147.

Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350.

Ong et al., "Stable Isotope Labeling by Amino Acids in Cell Culture, SILAC, as a Simple and Accurate Approach to Expression Proteomics", Molecular and Cellular Proteomics, vol. 1, 2002, pp. 376-386.

Oshima et al., "COX Selectivity and Animal Models for Colon Cancer", Current Pharmaceutical Design, vol. 8, 2002, pp. 1021-1034.

Ouguerram et al., "A New Labeling Approach Using Stable Isotopes to Study In Vivo Plasma Cholesterol Metabolism in Humans", Metabolism, vol. 51, No, 1, Jan. 2002, pp. 5-11.

Oyaizu et al., "Role of Apoptosis in HIV Disease Pathogenesis", J. of Clinical Immunology, vol. 15, No. 5, 1995, pp. 217-231.

Paku, S. "Origin and Structural Evolution of the Early Proliferating Oval Cells in Rat Liver", American Journal of Pathology, vol. 158, No. 4, Apr. 2001, pp. 1313-1323.

Palmer et al., "Telomere Length, Telomerase Activity, and Replicative Potential in HIV Infection: Analysis of CD4+ and CD8+ T Cells from HIV-discordant Monozygotic Twins", J. Experimental Medicine, vol. 185, No. 7, 1997, pp. 1381-1386.

Panteleo, Giuseppe, "Unraveling the Strands of HIV's Web", Nature Medicine, vol. 5, No. 1, 1999, pp. 27-28.

Extended European Search Report received for European Patent Application No. 06759050.5, mailed on Mar. 31, 2011, 7 pages.

Papageorgopoulos et al., "Toward the Measurement of Protein Synthesis by Mass Isotopomer Distribution Analysis (MIDA):Resolution of Isotopomers in a [d.sub.3 ]-Leucine Enriched Synthetic Oligopeptide Using Electrospray/Quadrupole Mass Spectrometry (ESI/MS)",Federation of American Societies for Experimental Biology, vol. 1022, 1993, p. A177.

Park et al., "Measurement of Small Intestinal Cell Turnover with [6,6, 2H2] Glucose", Berkeley Scientific, Abstract, vol. 1, No. 2, 1997, pp. 41-43.

Parks et al., "Carbohydrate-induced Hypertriacylglycerolemia: Historical Perspective and Review of Biological Mechanisms", Am. J. Nutr., vol. 71, 2000, pp. 412-433.

Parks et al., "Dependence of Plasma a-Tocopherol Flux on Very Low-Density Triglyceride Clearance in Humans", Free Radical Biology & Medicine, vol. 29, No. 11, 2000, pp. 1151-1159.

Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.

Paša-Tolic et al., "High Throughput Proteome-Wide Precision Measurements of Protein expression Using Mass Spectrometry", J. Am. Chem. Soc., vol. 121, 1999, pp. 7949-7950.

Patsalos et al., "Pattern of Myelin Breakdown During Sciatic Nerve Wallerian Degeneration: Reversal of the Order of Assembly", The Journal of Cell Biology, vol. 87, 1980, pp. 1-5.

Patterson et al., "Concentration Dependence of Methyl-Palmitate Isotope Ratios by Electron Impact Ionization Gas Chromatography/ Mass Spectrometry", Biol. Mass Spectrom., vol. 22, 1993, pp. 481-486.

Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.

Patton et al., "Measurements of Fatty Acid Synthesis by Incorporation of Deuterium from Deuterated Water", Biochemistry, vol. 18, No. 14, 1979, pp. 3186-3188.

Perelson et al., "Decay Characteristics of HIV-1-Infected Compartments During Combination Therapy", Nature 387, 1997, pp. 188-191.

Perelson et al., "HIV-1 Dynamics in Vivo: Virion Clearance Rate, Infected Cell Life-Span, and Viral Generation Time", Science, vol. 271, 1996, pp. 1582-1586.

Perochon et al., "Radiolabeling of the Lipids of Chinese Hamster Ovary Cells with the Probe 3-(Trifluoromethyl)-3-(m-[125]iodophenyl)diazirine", Analytical Biochemistry, vol. 254, 1997, pp. 109-118.

Previs et al., "Estimation of Protein Turnover In Vivo Using D2O", Diabetes Abstract Book, 61st Scientific Sessions, vol. 50, Supplement 2, A301, 2001, 1248-p.

Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.

Ramakers et al., "Chronic Suppression of Bioelectric Activity and Cell Survival in Primary Cultures of Rat Cerebral Cortex Biochemical Observations", European Journal of Neuroscience, vol. 3, No. 2, 1991, pp. 154-161.

Ravichandran et al., "In Vivo Labeling Studies on the Biosynthesis and Degradation of Collagen in Experimental Myocardial Infarction", Biochemistry Journal, vol. 24, No. 3, 1991, pp. 405-414.

Reichard, P., "From Deoxynucleotides to DNA Synthesis", Federation Proceedings, vol. 37, No. 1, 1978, pp. 9-14.

Reichard, P., "Interactions Between Deoxyribonucleotide and DNA Synthesis", Ann. Rev. Biochem. vol. 57, 1988, pp. 349-374.

Hellerstein et al., "Model for Measuring Absolute Rates of Hepatic de Novo Lipogenesis and Reesterification of Free Fatty Acids", The American Journal of Physiology, vol. 265, 1993, pp. E814-E820.

Hellerstein et al., "Subpopulations of Long-Lived and Short-Lived T Cells in Advanced HIV-1 Infection", The Journal of Clinical Investigation, vol. 112, No. 6, 2003, pp. 956-966.

Hellerstein et al., "T Cell Turnover in HIV-1 Disease", Immunity, vol. 7, 1997, pp. 583-589.

Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.

Hellerstein, M. K., "Measurement of T-Cell Kinetics: Recent Methodologic Advances", Trends Immunology Today, vol. 20, No. 10, 1999, pp. 438-441.

Hellerstein, M. K., "Methods for Measurement of Fatty Acid and Cholesterol Metabolism", Current Opinion in Lipidology,vol. 6, 1995, pp. 172-181.

Hellerstein, M. K., "New Stable Isotope-Mass Spectrometric Techniques for Measuring Fluxes through Intact Metabolic Pathways in Mammalian Systems: Introduction of Moving Pictures into Functional Genomics and Biochemical Phenotyping", Metabolic Engineering, vol. 6, 2004, pp. 85-100.

Hellerstein, M. K., "No Common Energy: de Novo Lipogenesis as the Road Less Traveled", The American Journal of Clinical Nutrition, vol. 74, 2001, pp. 707-708.

Hellerstein, M. K., "Synthesis of Fat in Response to Alterations in Diet: Insights from New Stable Isotope Methodologies", Lipids, vol. 31 (Supp), 1996, pp. S117-S125.

Hellerstein, M. K., "The Changing Face of Aids: Translators Needed", The American Journal of Clinical Nutrition, vol. 70, 1999, pp. 787-788.

Hellerstein, Marc K., "In Vivo Measurement of Fluxes Through Metabolic Pathways: The Missing Link in Functional Genomics and Pharaceutical Research", Annu. Rev. Nutr., vol. 3, 2003, pp. 379-402.

Ho et al., "Rapid Turnover of Plasma Virions and CD4 Lymphocytes in HIV-1 Infection", Nature, vol. 373, 1995, pp. 123-126.

Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.

Hsieh et al., "Dynamics of Keratinocytes in Vivo Using 2H2O Labeling: A Sensitive Marker of Epidermal Proliferation State", J Invest Dermatol, vol. 123, 2004, pp. 530-536.

Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.

Hudgins et al., "Relationship Between Carbohydrate-Induced Hypertriglyceridemia and Fatty Synthesis in Lean and Obese Subjects", J. Lipid Res., vol. 41, 2000, pp. 595-604.

Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.

Humphrey et al., "A New Method for the Measurement of Protein Turnover", Biochem. J., vol. 148, 1975, pp. 119-127.

Humphrey et al., "A Sensitive Method for Measuring Protein Turnover Based on the Measurement of 2-3H-labeled Amino Acids in Proteins", Biochem. J., vol. 156, 1976, pp. 561-568.

Iyengar et al., "Human Stools as a Source of Viable Colonic Epithelial Cells", The FASEB Journal, vol. 5, 1991, pp. 2856-2859.

James, J. S., "Clinical Implications of Virological Failure: Interview with Steven Deeks, M.D., San Francisco General Hospital", AIDS Treatment News, vol. 289, 1998, pp. 6-7.

Jennings et al., "The Use of Infrared Spectrophotometry for Measuring Body Water Spaces", Clinical Chemistry, vol. 45, No. 7, Jul. 1999, pp. 1077-1081.

Jones et al., "An Integrated 2H and 13C NMR Study of Gluconeogenesis and TCA Cycle Flux in Humans", American Journal of Physiology-Endocrinology and Metabolism, vol. 281, 2001, pp. E848-E856.

Jones et al., "Evidence for Diurnal Periodicity in Human Cholesterol Synthesis", Journal of Lipid Research, vol. 31, 1990, pp. 667-673.

Jung et al., "Metabolic Adaptations to Dietary Fat Malabsorption in Chylomicron-Deficient Mice", Biochem. J., vol. 343, 1999, pp. 473-478.

Jungas, "Fatty Acid Synthesis in Adipose Tissue Incubated in Tritiated Water", Biochemistry, vol. 7, No. 10, 1968, pp. 3708-3717.

Katz, "Futile Cycles in the Metabolism of Glucose", Curr. Top Cell Regul., vol. 10, 1976, pp. 237-289.

Kelleher et al., "Model Equations for Condensation Biosynthesis Using Stable Isotopes and Radioisotopes", Am. J. Physiol., vol. 262, 1992, pp. E118-E125.

Khairallah et al., "Assessment of Protein Turnover in Perfused Rat Liver: Evidence for Amino Acid Compartmentation from Differential Labeling of Free and tRNA-bound Valine", J Biol Chem, vol. 251, No. 5, 1976, pp. 1375-1384.

Kim et al., "A New Stable Isotope-Mass Spectrometric (MS) Method to Measure Proliferation Rates of Colon Epithelial Cells", Faseb Journal, vol. 14, No. 4, 2000, p. A718.

Lammert et al., "Effects of Isoenergetic Overfeeding of Either Carbohydrate or Fat in Young Men", British Journal of Nutrition, vol. 84, 2000, pp. 233-245.

Lee, "Cardiorespiratory Fitness, Body Composition, and All-Cause and Cardiovascular Disease Mortality in Men 1-3", Am. J. Clin. Nutr., vol. 69, 1999, pp. 373-380.

Lefebvre, "Naturally Labeled 13C-Glucose: A New Tool to Measure Oxidation Rates of Exogenous Glucose", Diabetes, vol. 28 (Suppl. 1), Jan. 1979, pp. 63-65.

Leung et al., "A Deficiency of Microsomal Triglyceride Transfer Protein Reduces Apolipoprotein B Secretion", The Journal of Biological Chemistry, vol. 275, No. 11, 2000, pp. 7515-7520.

Lewanczuk et al., "Comparison of the [13 C] Glucose Breath Test to the Hyperinsulinemic-Euglycemic Clamp When Determining Insulin Resistance", Diabetes Care, vol. 27, No. 2, 2004, pp. 441-447.

Lipkin, "Cell Proliferation Kinetics in the Gastrointestinal Tract of Man. I. Cell Renewal in Colon and Rectum", Journal of Clinical Investigations, vol. 42, No. 6, 1963, pp. 767-776.

Lipkin, "Proliferation and Differentiation of Normal and Diseased Gastrointestinal Cells", In Physiology of the Gastrointestinal Tract, L.R. Johnson ed., Raven Press, New York, 1987, pp. 255-284.

Lutton et al., "Critical analysis of the Use of 14C-acetate for Measuring In Vivo Rat Cholesterol Synthesis", Reprod. Nutr. Dev., vol. 30, 1990, pp. 71-84.

Macallan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.

Maentausta et al., "Radioimmunoassay of Conjugated Cholic Acid, Chenodeoxycholic Acid, and Deoxycholic Acid from Human Serum, with Use of 125I-Labeled Ligands", Clin. Chem., vol. 25, No. 2, 1979, pp. 264-268.

Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.

Margolick et al., "Failure of T-cell Homeostasis Preceding AIDS in HIV-1 Infection", Nature Medicine, vol. 1, No. 7, 1995, pp. 674-680.

Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.

Marin et al., "Dynamic Profiling of the Glucose Metabolic Network in Fasted Rat Hepatocytes using [1,2-13C2] Glucose", Biochemical Journal, vol. 381, 2004, pp. 287-294.

Martin et al., "Discovery of a Human Liver Glycogen Phosphorylase Inhibitor That Lowers Blood Glucose in Vivo", Proc. Natl. Acad. Sci. USA, vol. 95, No. 4, 1998, pp. 1776-1781.

Mathur-De Vre et al., "Molecular Aspects of Tritiated Water and Natural Water in Radiation Biology", Prog. Biophys. Molec. Biol., vol. 43, 1984, pp. 161-193.

McCloskey, "ElectronIonization Mass Spectra of Trimethylsilyl Derivatives of Nucleosides", Meth. Enz., vol. 193, 1990, pp. 825-841.

McCune et al., "Factors Influencing T-Cell Turnover in HIV-1-Seropositive Patients", J. Clin. Invest., vol. 105, 2000, pp. R1-R8.

McCune, J. M., "Thymic Function in HIV-1 Disease", Seminars in Immunology, vol. 9, 1997, pp. 397-404.

McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.

Boros et al., "Metabolic Profiling of Cell Growth and Death in Cancer: Applications in Drug Discovery", Drug Discovery Today, vol. 7, No. 6, Mar. 2002, pp. 364-372.

Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1088-1095.

Brown et al., "Treating Patients with Documented Atherosclerosis to National Cholesterol Education Program-Recommended Low-Density-Lipoprotein Cholesterol Goals with Atorvastatin, Fluvastatin, Lovastatin and Simvastatin", Journal of the American College of Cardiology, vol. 32, 1998, pp. 665-672.

Bucy et al., "Analysis of Lymph Node Biopsies in HIV Infected Patients Before and After HAART", 5th Conference on Retroviruses and Opportunistic Infections, Session 66, vol. 519, 1998, 177 Pages (Abstract only).

Caldwell et al., "Quantification of Peptide Isotopomer Abundances and Determination of Protein (sic) Turnover Rates by Using Mass Isotopomer Distribution Analysis", 41st Annual Amer. Society Mass Spectrometry on Mass Spectrometry, 1993, p. 331a (Abstract only).

Cassella et al., "Mechanisms of Lymphocyte Killing by HIV", Current Opinion in Hematology, vol. 4, 1997, pp. 24-31.

Cesar et al., "Direct Measurement of CD4+ and CD8+ T Cell Proliferation Rates in Vivo in AIDS Patients Using a Stable Isotope-Mass Spectrometric Technique", 5th Conference on Retroviruses and Opportunistic Infections, Chicago Illinois, 1998, Abstract only.

Chinkes et al., "Comparison of Mass Isotopomer Dilution Methods Used to Compute VLDL Production In Vivo", The American Journal of Physiology, vol. 271, 1996, pp. E373-E383.

Christiansen et al., "Effect of Dietary Energy Restriction on Glucose Production and Substrate Utilization in Type 2 Diabetes", Diabetes, vol. 49, Oct. 2000, pp. 1691-1699.

Clarke, R. B., "Isolation and Characterization of Human Mammary Stem Cells", Cell Proliferation, vol. 38, 2005, pp. 375-386.

Clayton, "Replication and Transcription of Vertebrate Mitochondrial DNA", Annual Review of Cell Biology, vol. 7, 1991, pp. 453-478.

Cohen et al., "Purine and Pyrimidine Metabolism in Human T Lymphocytes. Regulation of Deoxyribonucleotide Metabolism", The Journal of Biological Chemistry, vol. 258, No. 20, 1983, pp. 12334-12340.

Cohen, J. "Failure Isn't What It Used to Be . . . But Neither is Success", Science, vol. 279, 1998, pp. 1133-1134.

Collins et al., "A Method for Measuring Mitochondrial Proliferation In Vivo Using 2H20 Incorporation Into Mitochondria DNA", FASEB Journal, vol. 14, No. 4, Mar. 15, 2000, p. A620.

Collins et al., "Measurement of Mitochondrial DNA Synthesis In Vivo Using a Stable Isotope-Mass Spectrometric Technique", Journal of Applied Physiology, vol. 94, 2003, pp. 2203-2211.

Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, 1997, pp. 533-540.

Conrads et al., "Stable Isotope Labeling in Proteomics", The Synthesis Cambridge Isotope Laboratories, vol. 3, No. 2, Jan. 2002, pp. 1-3.

Craig et al., "The Impact of Physical Activity on Lipids, Lipoproteins, and Blood Pressure in Preadolescent Girls", Pediatrics, vol. 98, 1996, pp. 389-395.

Crain, "Preparation and Enzymatic Hydrolysis of DNA and RNA for Mass Spectrometry", Methods in Enzymology, vol. 193, 1990, pp. 782-790.

Dalvie, D. "Recent Advances in the Applications of Radioisotopes in Drug Metabolism, Toxicology and Pharmacokinetics", Current Pharmaceutical Design, vol. 6, 2000, pp. 1009-1028.

Davis et al., "Effect of Pinitol Treatment on Insulin Action in Subjects with Insulin Resistance", Diabetes Care, vol. 23, No. 7, Jul. 2000, pp. 1000-1005.

Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.

Deeks et al., "Viral Load and CD4+ T Cell Changes in Patients Failing Potent Protease Inhibitor Therapy", 5th Conference on Retroviruses and Opportunistic Infections, Session 53, vol. 419, 1998, p. 158 (Abstract only).

Dekker et al., "Glucose Homeostasis in Children with Falciparum Malaria: Precursor Supply Limits Gluconeogenesis and Glucose Production", J. Clin. Endocrinol. Metabol., vol. 82, 1997, pp. 2514-2521.

Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.

Dimitrov et al., "Scientific Correspondence", Nature, vol. 375, 1995, pp. 194-195.

Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.

Emken et al., "Incorporation of Deuterium-Labeled Trans- and CIS-13-Octadeconoic Acids in Human Plasma Lipids", Journal of Lipid Research, vol. 24, 1983, pp. 34-41.

Etnier et al., "Metabolism of Organically Bound Tritium in Man", Radiation Research, vol. 100, 1984, pp. 487-502.

Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.

Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.

Gasparini et al., "Amplification of DNA from Epithelial Cells in Urine", The New England Journal of Medicine, vol. 320, No. 12, 1989, p. 809.

Gerling et al., "Prediction of Liver Fibrosis According to Serum Collagen VI Level in Children with Cystic Fibrosis", The New England Journal of Medicine, vol. 336, No. 22, 1997, pp. 1611-1612.

Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.

Goz, "The Effects of Incorporation of 5-Halogenated Deoxyuridines into the DNA of Eukaryotic Cells", Pharmacological Reviews, vol. 29, 1977, pp. 249-272.

Gratzner, "Monoclonal Antibody to 5-Bromo- and 5-Iododeoxyuridine: A New Reagent for Detection of DNA Replication", Science, vol. 218, 1982, pp. 474-475.

Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.

Gygi et al., "Using Mass Spectrometry for Quantitative Proteomics", Proteomics: A Trends Guide, 2000, pp. 31-36.

Hansen et al., "A Practical Method for Uniform Isotopic Labeling of Recombinant Proteins in Mammalian Cells", Biochemistry, vol. 31, 1992, pp. 12713-12718.

Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.

Hellerstein, "Mass Isotopomer Distribution Analysis: A Technique for Measuring Biosynthesis and Turnover of Polymers", The American Journal of Physiology, vol. 263, 1992, pp. E988-E1001.

Hellerstein et al., "Altered Fluxes Responsible for Reduced Hepatic Glucose Production and Gluconeogenesis by Exogenous Glucose in Rats", The American Journal of Physiology, vol. 272, 1997, pp. E163-E172.

Hellerstein et al., "Directly Measured Kinetics of Circulating T Lymphocytes in Normal and HIV-1-Infected Humans", Nature Medicine, vol. 5, 1999, pp. 83-89.

Hellerstein et al., "Effects of Cigarette Smoking and its Cessation on Lipid Metabolism and Energy Expenditure in Heavy Smokers", J. Clin. Invest., vol. 93, 1994, pp. 265-272.

Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.

Hellerstein et al., "Hepatic Gluconeogenic Fluxes and Glycogen Turnover During Fasting in Humans. A Stable Isotope Study", The Journal of Clinical Investigation, vol. 100, No. 5, Sep. 1997, pp. 1305-1319.

Hellerstein et al., "Mass Isotopomer Distribution Analysis at Eight Years: Theoretical, Analytic, and Experimental Considerations", The American Journal of Physiology, vol. 276, 1999, pp. E1146-E1170.

Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.

Hellerstein et al., "Measurement of Hepatic Ra UDP-glucose in Vivo in Rats: Relation to Glycogen Deposition and Labeling Patterns", The American Journal of Physiology, vol. 272, 1997, pp. E155-E162.

Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology, Meeting, vol. 16, 2002, p. A256 (Abstract only).

Whittmann et al., "Application of MALDI-TOF MS to lysine-Producing Corynebacterium Glutamicum: A Novel Approach for Metabolic Flux Analysis", Eur. J. Biochem., vol. 268, 2001, pp. 2441-2455.

Winett et al., "Exercise Regimens for Men With HIV", JAMA, vol. 284, No. 2, 2000, pp. 175-176.

Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.

Wolfe, "Isotopic Measurement of Glucose and Lactate Kinetics", Ann. Med., vol. 22, 1990, pp. 163-170.

Wolfe et al., "Glucose Metabolism in Humans", ACS Symposium Series 258, Chapter 12, Turnund et al. ed., 1984, pp. 175-189.

Wolthers et al., "Rapid CD4+ T-Cell Turnover in HIV-1 Infection: A Paradigm Revisited", Immunology Today, vol. 19, No. 1, 1998, pp. 44-48.

Wolthers et al., "T Cell Telomere Length in HIV-1 Infection: No Evidence for Increased CD4+ T Cell Turnover", Science, vol. 274, 1996, pp. 1543-1547.

Wong et al., "From monoamines to genomic targets: a paradigm shift for drug discovery in depression", Nature Reviews Drug Discovery, vol. 3, Feb. 2004, pp. 136-151.

Wood et al., "Estimation of Pathways of Carbohydrate Metabolism", Biochemische Zeitschrift, vol. 338, 1963, pp. 809-847.

Zhang et al., "Deuterium NMR Study of the Origin of Hydrogen in Fatty Acids Produced In Vivo in Chicken.", European Journal of Lipid Science and Technology, vol. 108, 2006, pp. 125-133.

Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.

Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.

Pozharisski et al., "Study of Kinetics of Epithelial Cell Populations in Normal Tissues of the Rat's Intestines and in Carcinogenesis", Exp. Path., Bd., vol. 18, 1980, pp. 387-406.

Bantscheff et al., "Quantitative Mass Spectrometry in Proteomics: A Critical Review", Anal. Bioanal. Chem., vol. 389, No. 4, 2007, pp. 1017-1031.

Jones et al., "Modulation of Plasma Lipid Levels and Cholesterol Kinetics by Phytosterol Versus Phytostanol Esters", Journal of Lipid Research, vol. 41, 2000, pp. 697-705.

Sakurai, Y., "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.

Shen et al., "Purification of Oligodendrocyte and its Myelination to the Demyelinated Culture Model in Vitro", Acta Histochem Cytochem, vol. 35, No. 2, 2002, p. 123.

Tayek et al., "Glucose Production, Recycling, and Gluconeogenesis in Norrnials and Diabetics: a 1.iaSS isotopomer [U_13C] Glucose Study", 1996, pp. E709-E717.

Wang et al., "Validation of a Single-Isotope-Labeled Cholesterol Tracer Approach for Measuring Human Cholesterol Absorption", Lipids, vol. 39, No. 1, 2004, pp. 87-91.

Non Final Office Action received for U.S. Appl. No. 12/534,807, mailed on Mar. 18, 2011, 42 pages.

Notice of Allowance received for U.S. Appl. No. 12/534,807 mailed on Nov. 15, 2011, 10 pages.

Office Action received for Japanese Patent Application No. 2004-524832m mailed on Aug. 9, 2010, 10 pages.

Murphy et al., "A New, Sensitive in Vivo Diagnostic Test of Insulin Resistance: The Deuterated Oral Glucose Tolerance Test (2H-OGTT)", Diabetes, American Diabetes Association, US, vol. 53, No. 02, Jan. 1, 2004, 2 pages.

Written Opinion mailed Jul. 14, 2006, by the Australian Patent Office for Singapore patent application No. 200502593-7, filed on Nov. 4, 2003, 5 pages.

Australian Search Report and Written Opinion mailed Aug. 5, 2009, for SG Application No. 200717391-7, filed on May 3, 2006, 7 pages.

Supplementary Partial Search Report Received for European Patent Application No. 02806603.3, mailed on Jul. 25, 2006, 5 pages.

Supplementary Partial Search Report received for European Patent Application No. 03713429.3, mailed on Mar. 9, 2006, 6 pages.

Supplementary Partial Search Report received for European Patent Application No. 03749756.7, mailed on Aug. 17, 2005, 6 pages.

Supplementary Partial Search Report received for European Patent Application No. 03768624.3, mailed on Sep. 22, 2006, 4 pages.

Supplementary Search Report received for European Patent Application No. 04809469.2, mailed on Jul. 28, 2009, 4 pages.

Search Report received for European Patent Application No. 04812281.6, mailed on Oct. 6, 2010, 4 pages.

Supplementary Search Report received for European Patent Application No. 05725448.4, mailed on Jun. 30, 2009, 7 pages.

Extended European Search Report received for European Patent Application No. 06784805.1, mailed on Mar. 21, 2011, 7 pages.

Supplementary Search Report received for European Patent Application No. 05733311.4, mailed on Sep. 19, 2008, 9 pages.

International Search Report received for for PCT Patent Application No. PCT/US2003/004183, mailed on Jun. 29, 2004, 4 pages.

International Search Report received for for PCT Patent Application No. PCT/US2003/010554, mailed on Aug. 20, 2004, 4 pages.

International Search Report received for PCT Patent Application No. PCT/US2003/020052, mailed on Apr. 13, 2004, 3 pages.

International Search Report received for PCT Patent Application No. PCT/US2003/023340, mailed on Aug. 18, 2004, 4 pages.

International Search Report received for PCT Patent Application No. PCT/US2003/027623, mailed on Jul. 8, 2004, 4 pages.

International Search Report received for PCT Patent Application No. PCT/US2003/029361, mailed on Jan. 19, 2005, 4 pages.

International Search Report received for PCT Patent Application No. PCT/US2003/29526, mailed on Aug. 18, 2004, 3 pages.

International Search Report received for PCT Patent Application No. PCT/US2003/035107, mailed on Jul. 9, 2004, 2 pages.

International Search Report received for PCT Patent Application No. PCT/US2004/21063, mailed on Apr. 4, 2005, 2 pages.

International Search Report received for PCT Patent Application No. PCT/US2004/039722, mailed on Mar. 25, 2005, 3 pages.

International Search Report and Written Opinion received for PCT Patent Application No. PCT/US2005/005660, mailed on Oct. 11, 2007, 11 pages.

International Search Report and Written Opinion received for PCT Patent Application No. PCT/US2005/010429, mailed on Aug. 8, 2006, 15 pages.

International Search Report received for PCT Patent Application No. PCT/US2005/08265, mailed on Aug. 1, 2005, 4 pages.

International Search Report and Written Opinion received for PCT Patent Application No. PCT/US2006/017167, mailed on Feb. 5, 2008, 11 pages.

"NCBI Blast: Protein Sequence (17 letters)", Available at: <http://blast.ncbi.nlm.nih.gov/Blast.cgi>, Visited on May 29, 2008, 5 pages.

"New Diagnostic Technique Could Help Treat AIDS", Agence France-Presse, Dow Jones News, Feb. 17, 1998, pp. 1-2.

Zilversmit et al., "On the Calculation of 'Turnover Time' and 'Turnover Rate' from Experiments Involving the Use of Labeling Agents", J. of General Physiology, vol. 26, No. 3, 1943, pp. 325-331.

Ackermans et al., "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol", The Journal of Clinical Endocrinology & Metabolism, vol. 86, No. 5, 2001, pp. 2220-2226.

Adami et al., "The Aetiology and Pathogenesis of Human Breast Cancer", Mutation Research, vol. 333, 1995, pp. 29-35.

Airhart et al., "Compartmentation of Free Amino Acids for Protein Synthesis in Rat Liver", The Biochemical Journal, vol. 140, 1974, pp. 539-545.

Ajie et al., "In Vivo Study of the Biosynthesis of Long-Chain Fatty Acids Using Deuterated Water", The American Journal of Physiology, vol. 269, 1995, pp. E247-E252.

Anderson et al., "Direct HIV Cytopathicity Cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.

Antelo et al., "Adipose Triglyceride (TG) Turnover and De Novo Lipogenesis (DNL) in Humans: Measurement by Long-Term 2H2O Labeling and Mass Isotopomer Distribution Analysis (MIDA)", Experimental Biology, FASEB# 361.10, 2002, p. A400 (Abstract only).

Asher et al., "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine", Leukemia & Lymphoma, vol. 19, 1995, pp. 107-119.

Attardi et al., "Biogenesis of Mitochondria", Annual Review of Cell Biology, vol. 4, 1988, pp. 289-333.

Bach et al., "Stem Cells: The Intestinal Stem Cell as a Paradigm", Carcinogenesis, vol. 21, No. 3, 2000, pp. 469-476.

Backhouse et al., "Effects of Haloperidol on Cell Proliferation in the Early Postnatal Rat Brain", Neuropathology and Applied Neurobiology, vol. 8, No. 2, 1982, pp. 109-116.

Bandsma et al., "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile", The Biochemical Journal, vol. 329, 1998, pp. 699-703.

Bandsma et al., "The Contribution of Newly Synthesized Cholesterol to Bile Salt Synthesis in Rats Quantified by Mass Isotopomer Distribution Analysis", Biochemica et Biophysica Acta, vol. 1483, 2000, pp. 343-351.

Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.

Bickenbach, "Identification and Behavior of Label-Retaining Cells in Oral Mucosa and Skin", Journal of Dental Research, vol. 60, 1981, pp. 1611-1620.

Bier, D. M., "The Use of Stable Isotopes in Metabolic Investigation", Balliere's Clinical Endocrinology and Metabolism, vol. 1, No. 4, Nov. 1987, pp. 817-836.

Bier, D. M., "Stable Isotopes in Biosciences, their Measurement and Models for Amino Acid Metabolism", European Journal of Pediatrics, vol. 156, 1997, pp. S2-S8.

Bingham, Sheila A., "The Use of 24-h Urine Samples and Energy Expenditure to Validate Dietary Assessments", The American Journal of Clinical Nutrition, vol. 59(suppl), 1994, pp. 227S-231S.

Black et al., "Labeling DNA with Stable Isotopes: Economical and Practical Considerations", BioTechniques, vol. 30, 2001, pp. 134-138, 140.

Blair et al., "Changes in Physical Fitness and All-Cause Mortality. A Prospective Study of Healthy and Unhealthy Men", JAMA, vol. 273, 1995, pp. 1093-1098.

Blau et al., "Handbook of Derivatives for Chromatography", 2nd Edition, John Wiley & Sons Ltd., England, 1993.

Bonotto et al., "Study of the Distribution and Biological Effects of 3H in the Algae Acetabularia, Chlamydomonas and Porphyra", Current Topics in Radiation Research Quarterly, vol. 12, 1978, pp. 115-132.

Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.

* cited by examiner

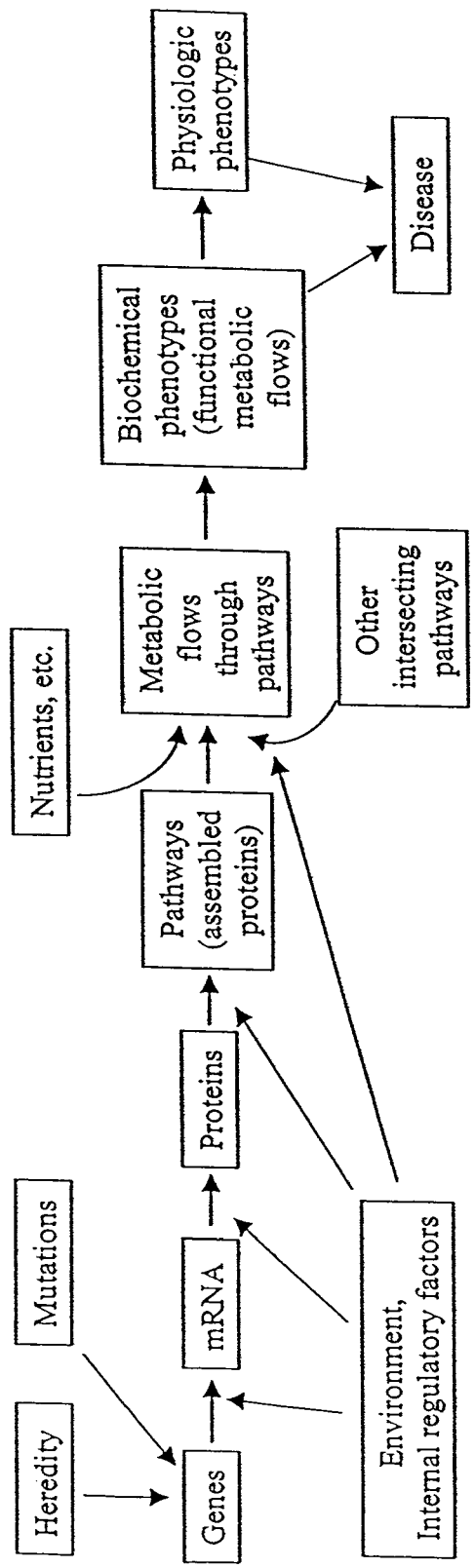
Fig. 1. From Gene to Protein to Phenotype and Disease: The Organization of Complex Biological Systems

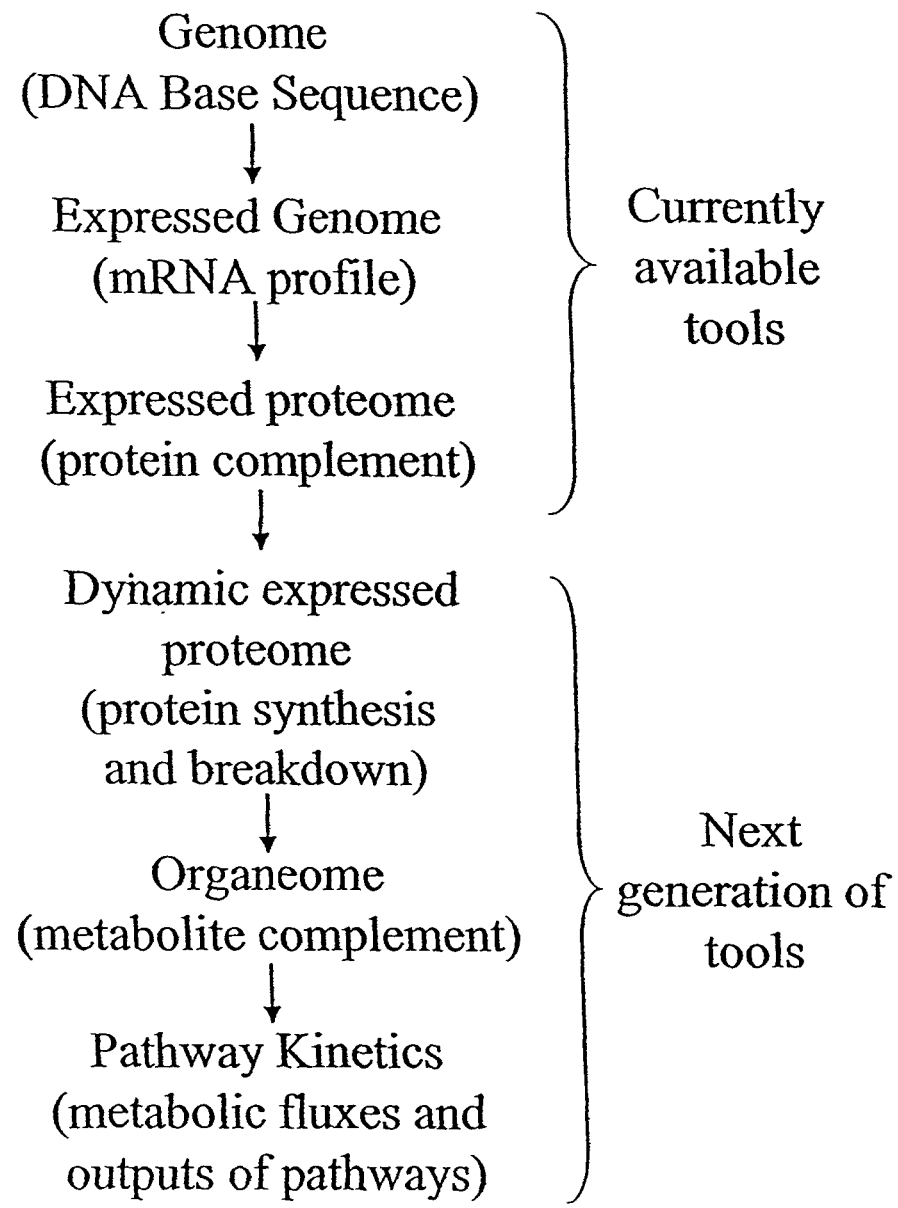
Fig. 2. Levels of "Functional Genomics"

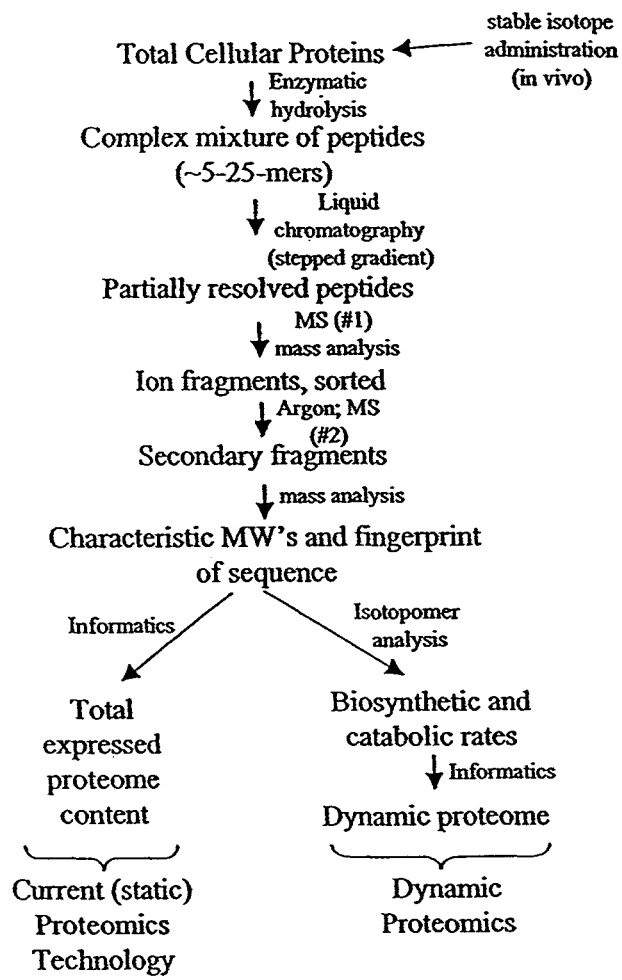
Fig. 3. Technique for Measuring Dynamic Proteomics

METHOD FOR AUTOMATED, LARGE-SCALE MEASUREMENT OF THE MOLECULAR FLUX RATES OF THE PROTEOME OR THE ORGANEOME USING MASS SPECTROMETRY

CROSS-REFERENCE TO RELATED APPLICATIONS

This application is a continuation of U.S. patent application Ser. No. 12/534,807 (now U.S. Pat. No. 8,129,335), filed Aug. 3, 2009, which is a continuation of U.S. patent application Ser. No. 10/523,250, filed Jan. 26, 2005, which is a U.S. National Phase Patent Application of International Application No. PCT/US2003/023340, filed Jul. 25, 2003, which claims priority to U.S. Provisional Patent Application Ser. No. 60/399,950 filed Jul. 30, 2002, all of which are hereby incorporated by reference in the present disclosure in their entireties.

FIELD OF THE INVENTION

The invention relates to methods for measuring molecular flux rates (synthesis and breakdown or input and removal rates from pools of molecules) in the proteome and the organeome (dynamic proteomics and dynamic organeomics, respectively) using mass spectrometry. The methods disclosed are capable of high-throughput, large-scale, automated applications. The methods are applicable to studies in genetics, functional genomics, drug discovery and development, drug toxicity, clinical diagnostics and patient management.

BACKGROUND OF THE INVENTION

Recent advances in the Human Genome project have, paradoxically, led to the wide-spread recognition of the inadequacy of gene sequence information by itself. Sequence information (i.e. structural genomics) is unlikely to generate insight into disease or normal physiology without better information concerning the functional consequence of genes. Higher levels of biological organization relative to gene sequences include expressed mRNA levels, the expressed protein complement and concentrations of organic molecules in metabolic pathways. These levels of cellular organization have been called gene expression profiling (transcriptomics), proteomics and organeomics, respectively. In aggregate, these can be seen as including the structural biochemical phenotype (i.e. the complete complement of molecules present) in a cell or organism.

Gene expression profiling of mRNA has been achieved through the development of gene expression chips. Such chips are available from companies such as Affymetrix. Enumerating the expressed genome (i.e. the complement of mRNA species), even in its entirety, however, does not ultimately provide information about biochemical function (phenotype) in a living system. Although impressive as a technology, gene expression chips do not solve the central problems of phenotype and function in biochemistry, which relate to the flow of molecules through the complex interactive network of proteins that comprise fully assembled living systems.

Other methods have focused on characterizing the complement of proteins in a living system, i.e. the "proteome." The most powerful technology for automated, large-scale characterization of expressed proteins (proteomics) to date has proven to be mass spectrometry. Mass spectrometers have greatly simplified large-scale automated proteome analysis. Analogous mass spectrometric methods have been advanced for the automated, large-scale characterization of organic metabolites (organeomics).

Many scientists in the pharmaceutical industry, including those in genomics companies, are predicting a log-jam of potential drug leads and targets that are under development. This log-jam arises from bottle-necks in the testing of phenotypic consequences of inhibiting particular targets—i.e. the "tail-end" of drug development. The tail-end of drug development (target validation) has not received a similar push from breakthrough technologies as the "front-end" (target identification and identification of chemical modulators of targets) of drug discovery.

One of the central problems in this area relates to the absence of routine, high-throughput dynamic measurements in biology and medicine. Just as biochemical phenotype is recognized to be reducible to the flow of molecules through metabolic pathways in complex catalytic networks, it is also widely recognized that most diseases reduce to an altered rate of a normal process. For example, atherogenesis reflects vascular wall proliferation and uptake of lipids; carcinogenesis reflects cell proliferation; infection can be characterized as microbial division, growth and death—this formulation is more informative than describing these disorders as alterations of static measures (e.g. concentrations of cholesterol, carcinogens, or bacteria). Yet rarely, if ever, are rates of biochemical processes measured in medical diagnostics. Static markers of dynamic processes are often helpful and may be better than nothing, but they are not the true measure of disease activity or disease risk. Nor do static measures allow for personalized biochemical monitoring. For example, each individual may have a different relationship between CD4 count and true turnover of T lymphocytes in HIV infection, or between DNA-adducts and the true risk of cancer, or between LDL cholesterol and the true rate of atherogenesis. In the final analysis, kinetic questions must be addressed by direct kinetic measurements.

Thus, the current art in mass spectrometric proteomics and organeomics is characterized by a shared and fundamental limitation: the information is static, not dynamic. Missing from both static proteomics and static organeomics is kinetics: fluxes into and out of the pools of molecules that are present in the system. Kinetics or dynamics differ from statics in the fundamental respect that the dimension of time is induded. Kinetics refers to the study of time-related changes in molecules whereas the concentrations of proteins or organic molecules determined in static measurements do not provide any information about their rates of change over time. Although the current techniques of static proteome and organeome characterization can provide a snapshot of what is present, these techniques cannot provide information concerning flows of molecules through the system (kinetics).

Thus, there is a tremendous need for the large scale determination of molecular flux rates of a plurality of proteins or organic metabolites—i.e. "dynamic proteomics" and "dynamic organeomics".

SUMMARY OF THE INVENTION

In order to meet these needs, the present invention is directed to a method of determining the molecular flux rates (i.e., the rates of synthesis or breakdown of a plurality of proteins in all or a portion of the proteome of a cell, tissue or organism). One or more isotope-labeled protein precursors are administered to a cell, tissue or organism for a period of time sufficient for one or more isotope labels to be incorporated into a plurality of proteins in the proteome or portion thereof of the cell, tissue or organism. The proteome or portion thereof are then obtained from the cell, tissue, or organism. A plurality of mass isotopomeric envelopes representing individual proteins in the proteome or portion of the proteome are then identified by mass spectrometry. In addition, the relative and absolute mass isotopomer abundances of the ions within the isotopomeric envelope corresponding to each identified protein are quantified by mass spectrometry. These relative and absolute mass isotopomer abundances allow the molecular flux rates of each identified protein to be calculated and the molecular flux rates of the plurality of proteins thereby to be determined.

In one aspect, the administering step may be continuous. The protein precursors may also be administered at regular measured intervals. The protein precursors may also be administered orally. The method may include the additional step of discontinuing the administering step.

The one or more protein precursors may be an amino acid, or may include one or more precursors such as $H_2O$, $CO_2$, $NH_3$, and $HCO_3$. Isotope label may include one or more isotopes such as $^2H$, $^{13}C$, $^{15}N$, $^{18}O$, $^{33}S$ and $^{34}S$. In a particular embodiment, the isotope label may be $^2H$.

In another aspect, the proteins may be modified prior to the measuring step. The modification may be by any method known in the art, such as biochemically degrading the proteins, or by chemically altering the proteins.

In a further aspect, the individual proteins may also be identified by both chromatography and mass spectrometry. In an additional embodiment, the plurality of proteins may also include the entire proteome of the cell, tissue, or organism. The calculated molecular flux rates of the proteins may be displayed after calculation.

The organism may be any organism in the art from cells in culture to living animals. In one aspect, the organism is a human.

In another aspect, the methods may further include administering a diagnostic or therapeutic agent to the cell, tissue, or organism prior to administering the isotope labeled precursor. The invention is also directed to a method of determining the effect of a diagnostic or therapeutic agent on a cell, tissue, or organism, by determining the molecular flux rates of a plurality of proteins in the cell, tissue, or organisms, administering the agent and again determining the molecular flux rates of the plurality of proteins in the cell, tissue or organism. The discovery and development of drugs can be achieved or facilitated by this means.

The methods may also include determining the effects of one or more genes on the molecular flux rates of synthesis of a plurality of proteins in a cell, tissue, or organism by determining the molecular flux rates of a plurality of proteins in a first population of one or more cells, tissues, or organisms that has one or more genes, determining the molecular flux rates on the plurality of proteins in a second population of one or more cells, tissues, or organisms that does not have the one or more genes, and comparing the molecular flux rates in the first and second populations to determine the effect of one or more genes on the molecular flux rates of a plurality of proteins.

In another aspect, the invention is drawn to determining the molecular flux rates of a plurality of organic metabolites in all or a portion of the organeome of a cell, tissue or organism. One or more isotope-labeled organic metabolites or organic metabolite precursors are administered to the cell, tissue or organism for a period of time sufficient for one or more isotope labels to be incorporated into a plurality of organic metabolites in the organeome or portion thereof of the cell, tissue or organism. The organeome or portion thereof is obtained from the cell, tissue, or organism. A plurality of mass isotopomeric envelopes of ions representing individual organic metabolites in the organeome or portion thereof are identified by mass spectrometry. In addition, the relative and absolute mass isotopomer abundances of the ions within the isotopic envelopes corresponding to each identified organic metabolite are quantified by mass spectrometry. These relative and absolute mass isotopomer abundances allow the rates of synthesis or removal of each identified organic metabolite to be calculated, and the molecular flux rates of the plurality of organic metabolites thereby to be determined.

In one aspect, one or more organic metabolites or organic metabolite precursors include one or more of $H_2O$, $CO_2$, $NH_3$, $HCO_3$, amino acids, monosaccharides, carbohydrates, lipids, fatty acids, nucleic acids, glycolytic intermediates, acetic acid, and tricarboxylic acid cycle intermediates. In another aspect, the isotope label includes $^2H$, $^{13}C$, $^{15}N$, $^{18}O$, $^{33}S$ or $^{34}S$. The plurality of organic metabolite precursors may include the entire organeome. The organism may be any known organism, including a human. In a particular embodiment, the isotope label may be $^2H$.

In another aspect, the administration of precursors may be continuous. Alternatively, the precursor may be administered at regular measured intervals. The one or more organic metabolites or organic metabolite precursors may be administered orally. Further, the method may include the additional step of discontinuing administration of the labeled precursor.

In an additional aspect, the method may include modifying organic metabolites prior to introduction into the mass spectrometer. The modification may be any method known in the art, such as biochemically degrading the organic metabolites or chemically altering the organic metabolites.

Individual organic metabolites in the organeome or portion thereof may be identified by mass spectrometry, and/or by chromatography. The calculated synthesis or removal rates of the plurality of organic metabolites may be displayed.

In another aspect, the invention is drawn to methods of administering a diagnostic or therapeutic agent to the cell, tissue, or organism prior to administering the precursor. In one embodiment, the invention is drawn to a method of determining the effect of a diagnostic or therapeutic agent on a cell, tissue, or organism by determining the rates of synthesis or removal of a plurality of organic metabolites in the cell, tissue, or organism, administering an agent, and determining the rates of synthesis or removal on the plurality of organic metabolites in the cell, tissue or organism. By this means, drug discovery and development may be facilitated or achieved.

In another aspect, the invention is drawn to a method of determining the effects of one or more genes on the molecular flux rates of a plurality of organic metabolites in a cell, tissue, or organism by determining the molecular flux rates of a plurality of organic metabolites in a first population of one or more cells, tissues, or organisms having One or more genes; determining the molecular flux rates of the plurality of organic metabolites in a second population of one or more cells, tissues, or organisms that do not include the one or more genes, and comparing the molecular flux rates of said plurality of organic metabolites in the first and second populations.

BRIEF DESCRIPTION OF THE DRAWINGS

FIG. 1 shows a schematic diagram illustrating the organization of complex biological systems.

FIG. 2 shows levels of functional genomics.

FIG. 3 shows techniques for measuring dynamic proteomics.

DETAILED DESCRIPTION OF THE INVENTION

Figure 4A:
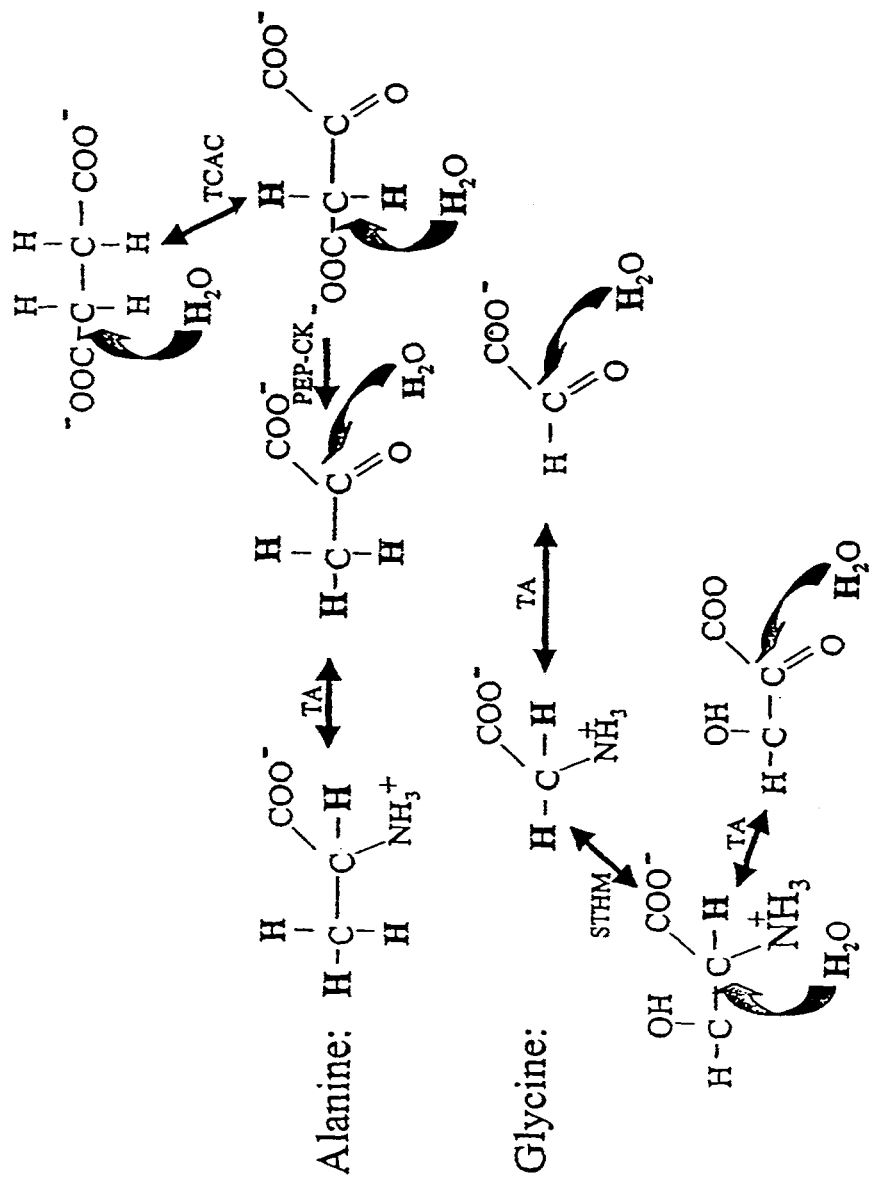
FIG. 4 depicts pathways of labeled hydrogen exchange from labeled water into selected free amino acids. Two nonessential amino adds (alanine, glycine) and an essential amino acid (leucine) are shown, by way of example. Alanine and glycine are presented in FIG. 4A. Leucine is presented in FIG. 4B. Abbreviations: TA, transaminase; PEP-CK, phosphoenol-pyruvate carboxykinase; TCAC, tricarboxylic acid cycle; STHM, serine tetrahydrofolate methyl transferase.
FIG. 4C depicts $H_2^{18}O$ labeling of free amino acids for protein synthesis.

The inventor has discovered a method of determining molecular flux rates (i.e., synthesis, breakdown and removal rates) of a plurality of proteins or a plurality of organic metabolites. First, an isotope-labeled precursor molecule is administered to a cell, tissue, or organism. The molecular flux rates of a plurality of proteins or a plurality of organic metabolites are then determined.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology, Humana Press; Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) 3. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Cabs, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); and *Mass isotopomer distribution analysis at eight years: theoretical, analytic and experimental considerations* by Hellerstein and Neese (*Am J Physiol* 276 (*Endocrinol Metab*. 39) E1146-E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, Mass isotopomer distribution analysis at eight years: theoretical, analytic and experimental considerations by Hellerstein and Neese (*Am J Physiol* 276 (*Endocrinol Metab*. 39) E1146-E1162, 1999). As appropriate, procedures involving the use of commercially available kits and reagents are generally carried out in accordance with manufacturer defined protocols and/or parameters unless otherwise noted.

"Molecular flux rates" refers to the rate of synthesis and/or breakdown of a protein and/or organic metabolite. "Molecular flux rates" also refers to a protein and/or organic metabolite's input into or removal from a pool of molecules, and is therefore synonymous with the flow into and out of said pool of molecules.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue usually includes of a family of isotopic isomers (isotopomers) which differ by the location of the isotopes on the molecule (e.g., $CH_3NHD$ and $CH_2DNH_2$ are the same isotopologue but are different isotopomers).

"Isotope-labeled water" includes water labeled with one or more specific heavy isotopes of either hydrogen or oxygen. Specific examples of isotope-labeled water include $^2H_2O$, $^3H_2O$, and $H_2^{18}O$.

"Protein Precursor" refers to any organic or inorganic molecule or component thereof, wherein one or more atoms of which are capable of being incorporated into protein molecules in cell, tissue, organism, or other biological system, through the biochemical processes of the cell, tissue, or organism. Examples of protein precursors include, but are not limited to, amino acids, $H_2O$, $CO_2$, $NH_3$, and $HCO_3$.

"Isotope Labeled protein precursor" refers to a protein precursor that contains an isotope of an element that differs from the most abundant isotope of the element present in nature, cells, tissue, or organisms. The isotope label may include specific heavy isotopes of elements present in biomolecules, such as $^2H$, $^{13}C$, $^{15}N$, $^{18}O$, $^{33}S$, $^{34}S$, or may contain other isotopes of elements present in biomolecules such as $^3H$, $^{14}C$, $^{35}S$, $^{125}I$, $^{131}I$. Isotope labeled protein precursors include; but are not limited to $^2H_2O$, $^{15}NH_3$, $^{13}CO_2$, $H^{13}CO_3$, $^2H$-labeled amino acids, $^{13}C$ labeled amino acids, $^{15}N$ labeled amino acids, $^{18}O$ labeled amino acids, $^{34}S$ or $^{33}S$ labeled amino acids, $^3H_2O$ $^3H$-labeled amino acids, and $^{14}C$ labeled amino acids.

"Isotope-labeled organic metabolite precursors" refer to an organic metabolite precursor that contains an isotope of an element that differs from the most abundant isotope of said element present in nature or cells, tissues, or organisms. Isotopic labels include specific heavy isotopes of elements, present in biomolecules, such as $^2H$, $^{13}C$, $^{15}N$, $^{18}O$, $^{35}S$, $^{34}S$, or may contain other isotopes of elements present in biomolecules, such as $^3H$, $^{14}C$, $^{35}S$, $^{125}I$, $^{131}I$. Isotope labeled organic metabolite precursors include but are not limited to $^2H_2O$, $^{15}NH_3$, $^{13}CO_2$, $H^{13}CO_3$, $^2H$-labeled amino acids, $^{13}C$-labeled amino acids, $^{15}N$-labeled amino acids, $^{18}O$-labeled amino acids, $^{33}S$ or $^{34}S$-labeled amino acids, $^3H_2O$, $^3H$-labeled amino acids, $^{14}C$-labeled amino acids, $^{14}CO_2$, and $H^{14}CO_2$.

"Partially purifying" refers to methods of removing one or more components of a mixture of other similar compounds. For example, "partially purifying a protein" refers to removing one or more proteins from a mixture of one or more proteins.

"Isolating" refers to separating one compound from a mixture of compounds. For example, "isolating a protein" refers to separating one specific protein from all other proteins in a mixture of one or more proteins.

A "biological sample" encompasses any sample obtained from a cell, tissue, or organism. The definition encompasses blood and other liquid samples of biological origin, that are accessible from an organism through sampling by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or organic metabolites. The term "biological sample" also encompasses a clinical sample such as serum, plasma, other biological fluid, or tissue samples, and also includes cells in culture, cell supernatants and cell lysates.

"Biological fluid" refers, but is not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

"Exact mass" refers to mass calculated by summing the exact masses of all the isotopes in the formula of a molecule (e.g. 32.04847 for $CH_3NHD$).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g. $CH_3NHD$, $^{13}CH_3NH_2$, $CH_3{}^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3{}^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e. "positional isotopomers" are not distinguished).

"Mass isotopomer envelope" refers to the set of mass isotopomers associated with a molecule or ion fragment.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonomously with the term "mass isotopomer pattern."

"Monoisotopic mass" refers to the exact mass of the molecular species that contains all $^1H$, $^{12}C$, $^{14}N$, $^{16}O$, $^{32}S$, etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as $m_0$ and the masses of other mass isotopomers are identified by their mass differences from $m_0$ ($m_1$, $m_2$, etc.).

"Isotopically perturbed" refers to the state of an element or molecule that results from the explicit incorporation of an element or molecule with a distribution of isotopes that differs from the distribution found in nature, whether a naturally less abundant isotope is present in excess (enriched) or in deficit (depleted).

"Monomer" refers to a chemical unit that combines during the synthesis of a polymer and which is present two or more times in the polymer.

"Polymer" refers to a molecule synthesized from and containing two or more repeats of a monomer.

"Protein" refers to a polymer of amino acids. As used herein, a "protein" may be to a long amino acid polymers as well as short polymers such as peptides.

"Proteome" refers to the complement of proteins expressed by a cell, tissue or organism under a specific set of conditions.

"Static proteomics" refers to current mass spectrometric techniques well-known in the art for characterizing the protein complement expressed in a cell, tissue or organism by their concentrations or levels but not as the rates of synthesis or breakdown (fluxes) of these proteins (to be contrasted with Dynamic Proteomics).

"Dynamic proteomics" refers to mass spectrometric techniques for characterizing the rates of synthesis and/or breakdown (fluxes) of the proteins in a proteome.

"Organic metabolite" refers to any organic molecule involved in metabolism in a cell, tissue, or organism. Organic metabolites may include, but are not limited to, amino acids, sugars, sugar alcohols, organic acids, sterols, and nucleotide bases.

"Organeome" refers to the population of organic molecules present in a cell, tissue or organism. "Organeome" may also refer to the population of organic molecules present in a cell, tissue or organism under a specific set of conditions.

"Static organeomics" refers to current mass spectrometric techniques well known in the art for characterizing the complement of organic molecules or metabolites present in a cell, tissue or organism by their concentrations or levels, but not by the rates of synthesis or breakdown of these organic molecules or metabolites.

"Dynamic organeomics" refers mass spectrometric techniques for characterizing the rates of synthesis and/or breakdown of the organic molecules or metabolites in an organeome.

"Organic metabolite precursor" refers to an organic or inorganic molecule capable of entering into cellular pools of organic metabolites either directly or by prior transformation.

III. Methods of the Invention

The present invention is directed to methods of determining the molecular flux rates of a plurality of proteins in all or a portion of the proteome of a cell, tissue or organism. First, one or more isotope-labeled protein precursors are administered to a cell, tissue or organism for a period of time sufficient to be incorporated into a plurality of proteins in the proteome or portion thereof. The proteome or portion thereof is obtained from the cell, tissue, or organism, and a plurality of individual proteins are identified by mass spectrometry. The relative and absolute mass isotopomer abundances of the ions within the isotopomeric envelope corresponding to each identified protein or peptide are quantified by mass spectrometry, and the molecular flux rates of each identified protein or peptide of said plurality of proteins can be determined.

The same methodology may be applied to determine the molecular flux rates of a plurality of organic metabolites in all or a portion of the organeome.

The organization of complex biological systems is illustrated in FIG. 1. The levels of functional genomics are illustrated in FIG. 2. The present invention is directed to methods of measuring, analyzing, quantitating, qualitating and interpreting dynamic proteomic measurements and dynamic organeomic measurements. (See FIG. 3).

Administering Isotope-Labeled Precursor(s)

As a first step in the methods of the invention, isotope-labeled precursors are administered.

A. Administering an Isotope-Labeled Precursor Molecule

1. Labeled Precursor Molecules a. Isotope Labels

The first step in measuring molecular flux rates involves administering an isotope-labeled precursor molecule to a cell, tissue, or organism. The isotope labeled precursor molecule may be a stable isotope or radioisotope. Isotope labels that can be used include, but are not limited to, $^2$H, $^{13}$C, $^{15}$N, $^{18}$O, $^3$H, $^{14}$C, $^{35}$S, $^{32}$P, $^{125}$I, $^{131}$I, or other isotopes of elements present in organic systems.

In one embodiment, the isotope label is $^2$H.

b. Precursor Molecules

The precursor molecule may be any molecule having an isotope label that is incorporated into a protein or organic metabolite. Isotope labels may be used to modify all precursor molecules disclosed herein to form isotope-labeled precursor molecules.

The entire precursor molecule may be incorporated into one or more proteins and/or organic metabolites. Alternatively, a portion of the precursor molecule may be incorporated into one or more proteins and/or organic metabolite.

Precursor molecules may include, but not limited to, $CO_2$, $NH_3$, glucose, lactate, $H_2O$, acetate, and fatty acids.

i. Protein Precursors

A protein precursor molecule may be any protein precursor molecule known in the art. These precursor molecules may be $CO_2$, $NH_3$, glucose, lactate, $H_2O$, acetate, and fatty acids.

Precursor molecules of proteins may also include one or more amino acids. The precursor may be any amino acid. The precursor molecule may be a singly or multiply deuterated amino acid. For example, the precursor molecule may be one or more of $^{13}$C-lysine, $^{15}$N-histidine, $^{13}$C-serine, $^{13}$C-glycine, $^2$H-leucine, $^{15}$N-glycine, $^{13}$C-leucine, $^2$H$_5$-histidine, and any deuterated amino acid. Labeled amino acids may be administered, for example, undiluted or diluted with non-labeled amino acids. All isotope labeled precursors may be purchased commercially, for example, from Cambridge Isotope Labs (Andover, Mass.).

Protein precursor molecules may also include any precursor for post-translational or pre-translationally modified amino acids. These precursors include but are not limited to precursors of methylation such as glycine, serine or $H_2O$; precursors of hydroxylation, such as $H_2O$ or $O_2$; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^2$H$_2$O in body water may be identified. The total number of C—H bonds in each non essential amino acid is known—e.g. 4 in alanine, 2 in glycine, etc.

The precursor molecule for proteins may be water. The hydrogen atoms on C—H bonds are the hydrogen atoms on amino acids that are useful for measuring protein synthesis from $^2$H$_2$O since the O—H and N—H bonds of proteins are labile in aqueous solution. As such, the exchange of $^2$H-label from $^2$H$_2$O into O—H or N—H bonds occurs without the synthesis of proteins from free amino acids as described above. C—H bonds undergo incorporation from $H_2O$ into free amino acids during specific enzyme-catalyzed intermediary metabolic reactions (FIG. 4). The presence of $^2$H-label in C—H bonds of protein-bound amino acids after $^2$H$_2$O administration therefore means that the protein was assembled from amino acids that were in the free form during the period of $^2$H$_2$O exposure—i.e. that the protein is newly synthesized. Analytically, the amino add derivative used must contain all the C—H bonds but must remove all potentially contaminating N—H and O—H bonds.

Figure 4B:
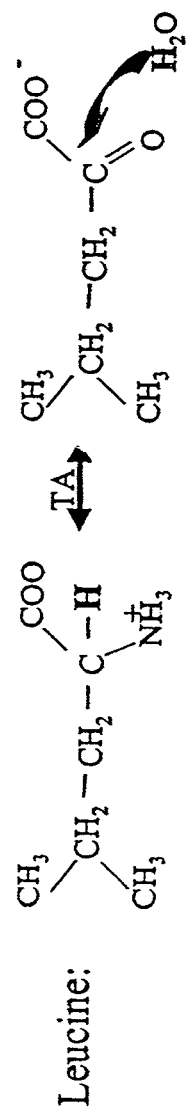

Hydrogen atoms from body water may be incorporated into free amino acids. $^2$H or $^3$H from labeled water can enter into free amino adds in the cell through the reactions of intermediary metabolism, but $^2$H or $^3$H cannot enter into amino acids that are present in peptide bonds or that are bound to transfer RNA. Free essential amino acids may incorporate a single hydrogen atom from body water into the α-carbon C—H bond, through rapidly reversible transamination reactions (FIG. 4). Free non-essential amino adds contain a larger number of metabolically exchangeable C—H bonds, of course, and are therefore expected to exhibit higher isotopic enrichment values per molecule from $^2$H$_2$O in newly synthesized proteins (FIGS. 4A-B).

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histine, the hydroxyl group in hydroxyproline or hydroxylysine, and others. Other amino adds synthesis pathways are known to those of skill in the art.

Figure 4C:
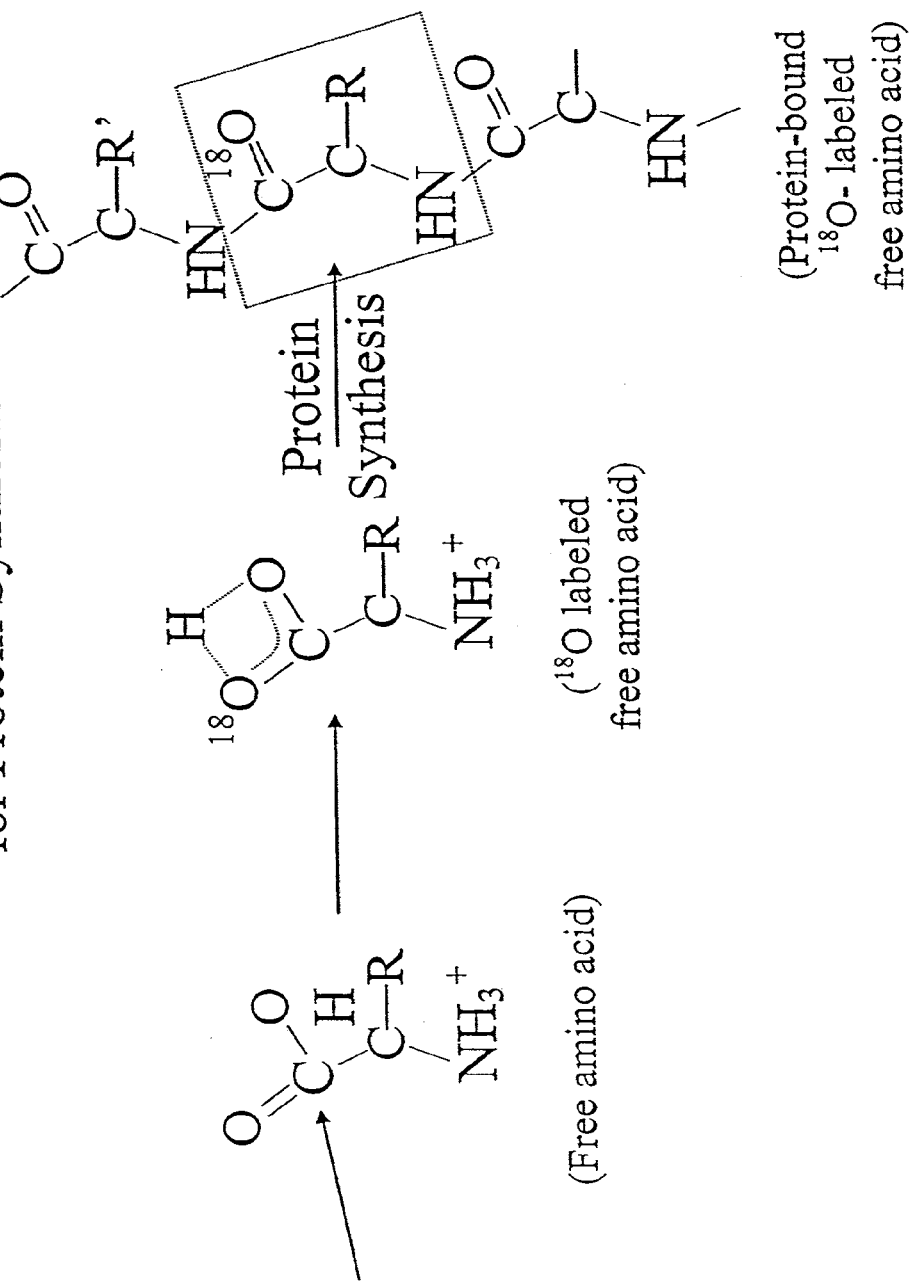

Oxygen atoms ($H_2^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art as illustrated in FIG. 4C. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g. methylation, hydroxylation, phosphorylation, prenylation, sulfation, carboxylation, acetylation or other known post-translational modifications).

Protein precursors for that are suitable for administration into a subject include, but are not limited to $H_2O$, $CO_2$, $NH_3$ and $HCO_3$, in addition to the standard amino acids found in proteins.

ii. Precursors of Organic Metabolites

Precursors of organic metabolites may be any precursor molecule capable of entering into the organic metabolite pathway. Organic metabolites and organic metabolite precursors include $H_2O$, $CO_2$, $NH_3$, $HCO_3$, amino acids, monosaccharides, carbohydrates, lipids, fatty acids, nucleic acids, glycolytic intermediates, acetic acid, and tricarboxylic acid cycle intermediates.

Organic metabolite precursors may also be administered directly. Mass isotopes may be useful in mass isotope labeling of protein or organic metabolite precursors include, but are not limited to $^2H$, $^{13}C$, $^{15}N$, $^{18}O$, $^{33}S$ and $^{34}S$. It is often desirable, in order to avoid metabolic loss of isotope labels, that the isotope-labeled atom(s) be relatively non-labile or at least behave in a predictable manner within the subject. By administering the isotope-labeled precursors to the biosynthetic pool, the isotope-labeled precursors can become directly incorporated into organic metabolites formed in the pool.

iii. Water as a Precursor Molecule

Water is a precursor of proteins and many organic metabolites. As such, labeled water may serve as a precursor in the methods taught herein.

Labeled water may be readily obtained commercially. For example, $^2H_2O$ may be purchased from Cambridge Isotope Labs (Andover, Mass.), and $^3H_2O$ may be purchased, e.g., from New England Nuclear, Inc. In general, $^2H_2O$ is non-radioactive and thus, presents fewer toxicity concerns than radioactive $^3H_2O$. $^2H_2O$ may be administered, for example, as a percent of total body water, e.g., 1% of total body water consumed (e.g., for 3 litres water consumed per day, 30 microliters $^2H_2O$ is consumed). If $^3H_2O$ is utilized, then a non-toxic amount, which is readily determined by those of skill in the art, is administered.

Relatively high body water enrichments of $^2H_2O$ (e.g., 1-10% of the total body water is labeled) may be achieved relatively inexpensively using the techniques of the invention. This water enrichment is relatively constant and stable as these levels are maintained for weeks or months in humans and in experimental animals without any evidence of toxicity. This finding in a large number of human subjects (>100 people) is contrary to previous concerns about vestibular toxicities at high doses of $^2H_2O$. The Applicant has discovered that as long as rapid changes in body water enrichment are prevented (e.g., by initial administration in small, divided doses), high body water enrichments of $^2H_2O$ can be maintained with no toxicities. For example, the low expense of commercially available $^2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool (FIG. 4A-B), than for 12 hours labeling of $^2H$-leucine at 10% free leucine enrichment, and thus 7-8% enrichment in leucine precursor pool for that period).

Relatively high and relatively constant body water enrichments for administration of $H_2^{18}O$ may also be accomplished, since the $^{18}O$ isotope is not toxic, and does not present a significant health risk as a result (FIG. 4C).

iv. Modes of Administering Precursors of Proteins and Organic Metabolites

Modes of administering the one or more isotope-labeled precursors may vary, depending upon the absorptive properties of the isotope-labeled precursor and the specific biosynthetic pool into which each compound is targeted. Precursors may be administered to organisms, plants and animals including humans directly for in vivo analysis. In addition, precursors may be administered in vitro to living cells. Specific types of living cells include hepatocytes, adipocytes, myocytes, fibroblasts, neurons, pancreatic β-cells, intestinal epithelial cells, leukocytes, lymphocytes, erythrocytes, microbial cells and any other cell-type that can be maintained alive and functional in vitro.

Generally, an appropriate mode of administration is one that produces a steady state level of precursor within the biosynthetic pool and/or in a reservoir supplying such a pool for at least a transient period of time. Intravenous or oral routes of administration are commonly used to administer such precursors to organisms, including humans. Other routes of administration, such as subcutaneous or intra-muscular administration, optionally when used in conjunction with slow release precursor compositions, are also appropriate. Compositions for injection are generally prepared in sterile pharmaceutical excipients.

B. Obtaining a Plurality of Proteins or Organic Metabolites

In practicing the method of the invention, in one aspect, proteins and organic metabolites are obtained from a cell, tissue, or organism according to the methods known in the art. The methods may be specific to the proteins or organic metabolites of interest. Proteins and organic metabolites of interest may be isolated from a biological sample.

A plurality of proteins or a plurality of organic metabolites may be acquired from the cell, tissue, or organism. The one or more biological samples may be obtained, for example, by blood draw, urine collection, biopsy, or other methods known in the art. The one or more biological sample may be one or more biological fluids. The protein or organic metabolite may also be obtained from specific organs or tissues, such as muscle, liver, adrenal tissue, prostate tissue, endometrial tissue, blood, skin, and breast tissue. Proteins or organic metabolites may be obtained from a specific group of cells, such as tumor cells or fibroblast cells. Proteins or organic metabolites also may be obtained, and optionally partially purified or isolated, from the biological sample using standard biochemical methods known in the art.

The frequency of biological sampling can vary depending on different factors. Such factors include, but are not limited to, the nature of the proteins or organic metabolites, ease and safety of sampling, synthesis and breakdown/removal rates of the proteins or organic metabolites from which it was derived, and the half-life of a therapeutic agent or biological agent.

The proteins or organic metabolites may also be purified partially, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the proteins or organic metabolites may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase degradation). Hydrolysis or degradation may be conducted either before or after purification and/or isolation of the proteins or organic metabolites. The proteins or organic metabolites also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

C. Analysis

Presently available technologies (static proteomics) used to profile differences in expressed proteins measure only protein levels (concentrations) in a cell and do so at one point in time. Approaches include Global Proteome Mapping (using 2D technology and Mass Spectrometry), Differential Expression Analysis (using 2D/DIGE technology and Mass Spectrometry), and Expression Analysis (2D/DIGE, Mass Spectrometry and LC-based, or other novel technology). While RNA and protein expression "chips" can be used to rapidly detect biologically mediated resistance to a therapeutic agent in a variety of disease states, they fail to determine the rate of change of gene expression or protein turnover. The methods of the present invention allow determination of the rates of gene expression and molecular flux rates of a plurality of proteins, as well as the molecular flux rates of a plurality of organic metabolites, and their changes over time.

Mass Spectrometry

Isotopic enrichment in proteins and organic metabolites can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrrolysis-MS, liquid chromatography-MS, electrospray ionization-MS, matrix assisted laser desorption-time of flight-MS, Fourier-transform-ion-cyclotron-resonance-MS, and cycloidal-MS.

Mass spectrometers convert molecules such as proteins and organic metabolites into rapidly moving gaseous ions and separate them on the basis of their mass-to-charge ratios. The distributions of isotopes or isotopologues of ions, or ion fragments, may thus be used to measure the isotopic enrichment in a plurality of proteins or organic metabolites.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a protein, and then generate secondary fragments of the initial ions. The resulting overlapping sequences allows complete sequencing of the protein, by piecing together overlaying "pieces of the puzzle", based on a single mass spectrometric analysis within a few minutes (plus computer analysis time).

The MS/MS peptide fragmentation patterns and peptide exact molecular mass determinations generated by protein mass spectrometry provide unique information regarding the amino acid sequence of proteins and find use in the present invention. An unknown protein can be sequenced and identified in minutes, by a single mass spectrometric analytic run. The library of peptide sequences and protein fragmentation patterns that is now available provides the opportunity to identify components of complex proteome mixtures with near certainty.

Different ionization methods are also known in the art. One key advance has been the development of techniques for ionization of large, non-volatile macromolecules including proteins and polynucleotides. Techniques of this type have included electrospray ionization (ESI) and matrix assisted laser desorption (MALDI). These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS (or other mass spectrometric modalities that analyze ions of proteins and organic metabolites, rather than small inorganic gases) is used to measure mass isotopomer abundances of organic molecules, hydrogen-labeled isotope incorporation from isotope-labeled water is amplified 3 to 7-fold, depending on the number of hydrogen atoms incorporated into the organic molecule from isotope-labeled water in vivo.

In general, in order to determine a baseline mass isotopomer frequency distribution for the protein, such a sample is taken before infusion of an isotopically labeled precursor. Such a measurement is one means of establishing in the cell, tissue or organism, the naturally occurring frequency of mass isotopomers of the protein. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of $^{13}C$ present in organic carbon in 1.11%. Methods of determining such isotopomer frequency distributions are discussed below. Typically, samples of the protein are taken prior to and following administration of an isotopically labeled precursor to the subject and analyzed for isotopomer frequency as described below. Similar considerations apply to the isolation of organic molecules for Dynamic Organeomics.

Thus, a single analysis of even an enormously complex mixture of proteins (that has been subjected to proteolytic cleavage or analyzed directly) can uniquely identify peptides representing thousands of expressed proteins.

Proteins may also be detected using protein chips. Several commercial "protein chip" equivalents are now marketed, using mass spectrometry (e.g. Ciphergen Biosystems). The efficiency of peptide sequence determination by mass analysis, combined with powerful ion fragmentation technology (MS/MS instruments) and/or peptide generating biochemical methods (e.g. proteolysis), improvements in sample introduction methods (HPLC, surface desorption, etc.), improved capacity for ionization of even the largest macromolecules (ESI, MALDI/SELDI) and rapid computerized handling of large data sets and comparison to peptide/protein reference libraries, have made mass spectrometry a general and powerful tool for automated, large-scale, high-throughput static proteomics.

Identification of a Plurality of Proteins or Organic Molecules

The plurality of proteins or organic molecules is analyzed by mass spectrometry, using standard methods well known in the art. The following references describe the application of static mass spectrometric techniques to protein identification, with respect to proteome analysis in particular: Ideker T, Thorsson V, Ranish J A, Christmas R, Buhler J, Eng J K, Bumgarner R, Goodlett D R, Aebersold R, Hood L "Integrated genomic and proteomic analyses of a systemically perturbed metabolic network." Science. 2001 May 4; 292 (5518): 929-34; Gygi S P, Aebersold R. "Mass spectrometry and proteomics." Curr Opin Chem. Biol. 2000 October; 4 (5): 489-94; Gygi SP, Rist B, Aebersold R "Measuring gene expression by quantitative proteome analysis" Curr Opin Biotechnol. 2000 August; 11 (4): 396-401; Goodlett D R, Bruce J E, Anderson G A, Rist B, Pasatolic L, Fiehn O, Smith R D, Aebersold R. "Protein identification with a single accurate mass of a cysteine containing peptide and constrained database searching" Anal Chem. 2000 Mar. 15; 72 (6): 1112-8; and Goodlett D R, Aebersold R, Watts J D "Quantitative in vitro kinase reaction as a guide for phophoprotein analysis by mass spectrometry" Rapid Commun Mass Spectrom. 2000; 14 (5): 344-8; Zhou, H. et al (April 2001) Nature Biotechnol. 19: 375-378.

Protein biochips, also known as protein arrays or antibody arrays, are used to identify proteins. These biochips hold the potential to measure protein-protein interactions, protein-small molecule interactions, and enzyme-substrate reactions. They can also distinguish the proteins of a healthy cell from those of a diseased cell. Protein biochips draw on the DNA chip technology developed for genomics and are also able to analyze thousands of samples simultaneously. While the human genome may contain 100,000 genes, post-translational modifications and RNA splicing events result in far greater than 100,000 proteins.

Some biochips incorporate a type of mass spectrometry called surface enhanced laser desorption/ionization [SELDI], and biochip technology in a single, integrated platform, allowing the proteins to be captured, separated, and quantitatively analyzed directly on the chip. The chips are read directly by the SELDI process without radioactive or fluorescent labels or genetically engineered tags.

While these techniques are useful, they merely provide a static assessment of the proteome, not a dynamic assessment of the proteome. The methods herein provide such a dynamic assessment.

Identification of a Plurality of Organic Metabolites

The sample containing organic metabolites is analyzed by mass spectrometry, using standard methods well known in the art. The following reference describes the application of static mass spectrometric techniques to metabolite identification, with respect to organic metabolite identification: Wolfe, R. R. Radioactive and Stable Isotope Tracers in Biomedicine: Principles and Practice of Kinetic Analysis. John Wiley & Sons; (March 1992).

The pattern of intermediary metabolites and their concentrations in living systems represents a still-higher level of biochemical phenotype. Myriad organic molecules are present in living systems and serve as substrates for the enzymes that control flows through functional biochemical pathways. A plurality of organic metabolites may be most effectively accomplished by use of ESI-MS/MS or GC/MS approaches.

Spots of blood or urine are introduced into an MS device and characterized by chromatographic behavior and mass spectrum.

This approach has been used for diagnostic screening of urine samples for a wide range of organic metabolites to detect inborn errors of metabolism in children. Plant biochemists have also reported some metabolic profiling work concerning the functional biochemistry of plants.

Technically, it is easier to isolate organic metabolites than proteins using traditional mass spectrometers (e.g. GC/MS instruments) because organic metabolites are generally of smaller size and greater volatility than proteins. Other features of organeomics strongly support the potential applicability of mass spectrometry (e.g. a very large number of analytes that need to be measured concurrently; requirement to measure concentrations; the need for automation and complex data handling; and the need for comparison to informatics libraries).

Measuring Relative and Absolute Mass Isotopomer Abundances

Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the invention.

Calculating Labeled: Unlabeled Proportion of Proteins and Organic Metabolites

The proportion of labeled and unlabeled proteins or organic metabolites is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686; 5,910,403; and 6,010,846 which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety.

In addition to the above-cited references, calculation software implementing the method is publicly available from Professor Marc Hellerstein, University of California, Berkeley.

The comparison of excess molar ratios to the theoretical patterns can be carried out using a table generated for a protein of interest, or graphically, using determined relationships. From these comparisons, a value, such as the value p, is determined, which describes the probability of mass isotopic enrichment of a subunit in a precursor subunit pool. This enrichment is then used to determine a value, such as the value $A_x^*$, which describes the enrichment of newly synthesized proteins for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M_x$, $$\text{Fractional abundance of } M_x = A_x = \frac{\text{Abundance } M_x}{\sum_{i=0}^{n} \text{Abundance } M_i},$$

where 0 to n is the range of nominal masses relative to the lowest mass ($M_0$) mass isotopomer in which abundances occur.

$$\Delta \text{ Fractional abundance (enrichment or depletion)} =$$

$$(A_x)_e - (A_x)_b = \left(\frac{\text{Abundance } M_x}{\sum_{i=0}^{n} \text{Abundance } M_i}\right)_e - \left(\frac{\text{Abundance } M_x}{\sum_{i=0}^{n} \text{Abundance } M_i}\right)_b,$$

where subscript e refers to enriched and b refers to baseline or natural abundance.

In order to determine the fraction of polymers that were actually newly synthesized during a period of precursor administration, the measured excess molar ratio ($EM_x$) is compared to the calculated enrichment value, $A_x^*$, which describes the enrichment of newly synthesized biopolymers for each mass isotopomer, to reveal the isotopomer excess ratio which would be expected to be present, if all isotopomers were newly synthesized.

Calculating Molecular Flux Rates

The method of determining rate of synthesis includes calculating the proportion of mass isotopically labeled subunit present in the protein precursor pool, and using this proportion to calculate an expected frequency of a protein containing at least one mass isotopically labeled subunit. This expected frequency is then compared to the actual, experimentally determined protein isotopomer frequency. From these values, the proportion of protein which is synthesized from added isotopically labeled precursors during a selected incorporation period can be determined. Thus, the rate of synthesis during such a time period is also determined.

A precursor-product relationship is then applied. For the continuous labeling method, the isotopic enrichment is compared to asymptotic (i.e., maximal possible) enrichment and kinetic parameters (e.g., synthesis rates) are calculated from precursor-product equations. The fractional synthesis rate ($k_s$) may be determined by applying the continuous labeling, precursor-product formula:

$$k_s = [\ln(1-f)]/t,$$

where f=fractional synthesis=product enrichment/asymptotic precursor/enrichment and t=time of label administration of contacting in the system studied.

For the discontinuous labeling method, the rate of decline in isotope enrichment is calculated and the kinetic parameters of proteins are calculated from exponential decay equations. In practicing the method, biopolymers are enriched in mass isotopomers, preferably containing multiple mass isotopically labeled precursors. These higher mass isotopomers of the proteins, e.g., proteins containing 3 or 4 mass isotopically labeled precursors, are formed in negligible amounts in the absence of exogenous precursor, due to the relatively low abundance of natural mass isotopically labeled precursor, but are formed in significant amounts during the period of protein precursor incorporation. The proteins taken from the cell, tissue, or organism at the sequential time points are analyzed by mass spectrometry, to determine the relative frequencies of a high mass protein isotopomer. Since the high mass isotopomer is synthesized almost exclusively before the first time point, its decay between the two time points provides a direct measure of the rate of decay of the protein.

Preferably, the first time point is at least 2-3 hours after administration of precursor has ceased, depending on mode of administration, to ensure that the proportion of mass isotopically labeled subunit has decayed substantially from its highest level following precursor administration. In one embodiment, the following time points are typically 1-4 hours after the first time point, but this timing will depend upon the replacement rate of the biopolymer pool.

The rate of decay of the protein is determined from the decay curve for the three-isotope protein. In the present case, where the decay curve is defined by several time points, the decay kinetics can be determined by fitting the curve to an exponential decay curve, and from this, determining a decay constant.

Breakdown rate constants ($k_d$) may be calculated based on an exponential or other kinetic decay curve:

$$k_d = [-\ln f]/t.$$

While the invention has been described with respect to specific mass isotopes and proteins, it will be appreciated how the method can be used to determine subunit pool composition, and rates of synthesis and decay for substantially any biopolymer which is formed from two or more identical subunits which can be mass isotopically labeled. Similar considerations apply for organic metabolites.

Uses of the Techniques of the Present Invention

Examples of medically relevant metabolic determinations which can be made, using the methods of the invention include: i) molecular flux rates of proteins involved in fat or cholesterol synthesis in a cell, tissue, or organism, to determine nutritional effects and/or the effects of drug treatment; ii) molecular flux rates of plasma proteins, as may occur in certain disease states before, during and after treatment with various drugs; iii) muscle protein dynamics, to determine effects of such determinants as exercise, hormones, drug treatment, age and disease on synthesis and breakdown of muscle protein; iv) rates of protein synthesis, including viral replication rates in vivo, for assessment of antiviral drugs on such rates in vivo, and rates of protein synthesis and degradation in a tumor, to determine the efficacy of chemotherapy; v) study of changes in gluconeogenesis, as may be affected by diseases such as diabetes, cancer and hypoglycemia. Normal tissue and diseased tissue can often be distinguished by the types of active genes and their expression levels; furthermore, the progression of disease can be determined by knowing the rate of change of protein synthesis or breakdown. Such testing can be performed in vivo directly on human subjects or ex vivo using cell cultures. Cell cultures may include animal cells such as human cells, plant cells, microbial cells including fungi, yeast and bacteria.

Altered expression patterns of oncogenes and tumor suppressor genes, for example, are reflected in changes in the synthesis and/or breakdown rates of the proteins that they code, and can effect dramatic changes in the expression profiles of numerous other genes. Different protein turnover or organic metabolite fluxes can serve as markers of the transformed state and are, therefore, of potential value in the diagnosis and classification of tumors. Differences in gene expression, which are not the cause but rather the effect of transformation, may be used as markers for the tumor stage. Thus, the assessment of the protein kinetic consequences of known tumor-associated genes has the potential to provide meaningful information with respect to tumor type and stage, treatment methods, and prognosis. Furthermore, new tumor-associated genes may be identified by systemically correlating their functional consequences on protein or organic metabolite fluxes with their level of gene expression in tumor specimens and control tissue. Genes whose expression is increased or reduced in tumors relative to normal cells, in association with altered fluxes of proteins or organic metabolites, are candidates for classification as oncogenes, tumor suppressor genes or genes encoding apoptosis-inducing products. Generally, the underlying premise is that the profiles of dynamic protein or organic metabolite fluxes may provide more specific, direct and accurate markers of gene function than cruder, less biochemical and less systematic markers of phenotype can provide. By this means, the physiological function or malfunction of the gene product in the organism can be established—i.e. true "functional genomics" become possible.

These practical applications can help physicians reduce health care costs, achieve rapid therapeutic benefits, limit administration of ineffective yet toxic drugs, and monitor changes in (e.g., decreases in) pathogenic resistance.

Kits

The invention provides kits for measuring and comparing molecular flux rates in vivo. The kits may include isotope-labeled precursor molecules, and in preferred embodiments, chemical compounds known in the art for separating, purifying, or isolating proteins, and/or chemicals necessary to obtain a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for Obtaining samples from the cell, tissue, or organism (e.g., specimen cups, needles, syringes, and tissue sampling devices) may also be optionally provided.

ADVANTAGES OF THE PRESENT INVENTION

The field of the current invention relates to the measurement of Dynamic Proteomics and Dynamic Organeomics—the kinetics (i.e., the molecular flux rates—synthesis and breakdown rates; production and removal) of the expressed proteins and organic metabolites, respectively, in a living system. The capacity to measure static levels of very large numbers of proteins and organic metabolites at one time, by use of mass spectrometric or 2-dimensional gel electrophoresis profiling techniques, has greatly advanced the field of Static Proteomics and Organeomics. Missing from all current proteomic and organeomic measurements is a key element, however: kinetics or dynamic fluxes (i.e. rates of input and outflow of molecules, which brings in the dimension of time).

1) Differences from current mass spectrometric proteome profiling include:
   a) Current static mass spectrometric profiling techniques do not measure fluxes (kinetics or flow of molecules through pathways).
   b) The operational procedure of a prior step wherein stable isotope labels are administered in vivo or ex vivo, before collection of the biological sample, is not used or known in the field of profiling for proteomics and organeomics.
   c) The analytic procedure of monitoring particular mass isotopomers, measuring their quantitative abundances, and calculating individualized synthesis and turnover rates for each molecule based on its molecular formula, the stable isotope label added and mass isotopomer combinatorial calculations, has not been used in the field of proteomics and organeomics.
   d) By adding kinetics, the focus is changed fundamentally from concentrations of individual molecules to the control of pathway fluxes into and out of pools of molecules (i.e. to the true biochemical consequences of individual molecules on functional biochemical outputs).
   e) Kinetic measurements allow direct inference of regulatory steps controlling homeostasis of the proteome and organeome.
2) Fundamental advantages and/or surprising results that have emerged or may be expected:
   a) The translational (protein synthesis) program of a cell or organism can be immediately observed, without a lag phase for change in protein concentrations.
   b) The protein catabolic program of a cell or organism can be observed directly, which data is not otherwise available.
   c) The remarkable result has emerged that labeling of proteome has up to two orders of magnitude greater sensitivity than static measurements for detecting treatment effects (i.e. <200 proteins out of 20,000 show large changes in static concentrations at steady state after even the most potent interventions, whereas up to 40-50% of proteins show large changes in synthetic or catabolic rates at steady state after potent interventions).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the appended claims.

Applicants have not abandoned or dedicated to the public any unclaimed subject matter.

What is claimed is:

1. A method of determining the molecular flux rates of a plurality of proteins in a cell, tissue or organism, said method comprising:
   a) administering one or more isotope-labeled protein precursors to said cell, tissue or organism for a period of time sufficient for one or more isotope labels of the one or more isotope-labeled protein precursors to be incorporated into proteins in the cell, tissue or organism;
   b) obtaining a sample from the cell, tissue, or organism wherein the sample comprises a plurality of proteins;
   c) degrading the plurality of proteins to form a mixture of peptides from the plurality of proteins;
   d) performing a first mass spectrometry on the mixture of peptides from the plurality of proteins to identify a plurality of mass isotopomeric envelopes of an initial series of ionic fragments representing individual proteins;

e) performing a second mass spectrometry to identify secondary fragments of the initial series of ionic fragments;

f) comparing the initial series of ionic fragments identified by the first mass spectrometry with the secondary fragments identified by the second mass spectrometry to identify one or more of the individual proteins in the sample;

g) quantifying relative and absolute mass isotopomer abundances of the ionic fragments of one or more of the identified individual proteins within the mass isotopomeric envelope; and h) calculating the molecular flux rates of one or more of the identified individual proteins to determine the molecular flux rates of said plurality of proteins.

2. The method of claim 1, wherein said administering step (a) is continuous.

3. The method of claim 1, wherein said administering step (a) comprises administering said one or more protein precursors at regular measured intervals.

4. The method of claim 1, wherein said one or more isotope-labeled protein precursors are administered orally.

5. The method of claim 1, further comprising the step of displaying the molecular flux rates of one or more of the identified individual proteins of said plurality of proteins.

6. The method of claim 1, wherein said one or more isotope-labeled protein precursors is an isotope-labeled amino acid.

7. The method of claim 6, wherein the one or more isotope-labeled protein precursors are selected from the group consisting of isotope-labeled $H_2O$, isotope-labeled $CO_2$, isotope-labeled $NH_3$, and isotope-labeled $HCO_3$.

8. The method of claim 1, wherein said one or more isotope labels is selected from the group consisting of $^2H$, $^{13}C$, $^{15}N$, $^{18}O$, $^{33}S$ and $^{34}S$.

9. The method of claim 8, wherein said one or more isotope label is $^2H$.

10. The method of claim 1, wherein said one or more isotope-labeled protein precursor is selected from the group consisting of $^2H_2O$, $H_2^{18}O$, $^{13}CO_2$, $C^{18}O^{17}O$, $H^{16}CO_3$, $^{15}NH_3$, $^2H$-labeled amino acids, $^{13}C$-labeled amino acids, $^{15}N$-labeled amino acids, $^{18}O$-labeled amino acids, $^{34}S$-labeled amino acids, and $^{33}S$-labeled amino acids.

11. The method of claim 10, wherein said one or more isotope-labeled protein precursor is $^2H_2O$.

12. The method of claim 1, wherein the organism is a human.

13. The method of claim 1, further comprising administering a diagnostic or therapeutic agent to said cell, tissue, or organism prior to said administering step (a).

14. A method of determining the effects of one or more genes on the molecular flux rates of a plurality of proteins in a cell, tissue, or organism, comprising:

a) determining the molecular flux rates a plurality of proteins in a first population of one or more cells, tissues, or organisms according to the method of claim 1, wherein said cells, tissues, or organisms of said first population comprise said one or more genes;

b) determining the molecular flux rates of the plurality of proteins in a second population of one or more cells, tissues, or organisms according to the method of claim 1, wherein said second population does not comprise said one or more genes; and c) comparing the molecular flux rates in said first and second populations to determine the effect of one or more genes on the molecular flux rates of a plurality of proteins.

15. The method of claim 14, further comprising isolating a plurality of samples from said cell, tissue or organism.

16. The method of claim 1, further comprising isolating a plurality of samples from said cell, tissue or organism.

17. The method of claim 1, wherein the one or more isotope-labeled protein precursors is one or more stable isotope-labeled protein precursors.

18. The method of claim 1, wherein the one or more isotope-labeled protein precursors is selected from the group consisting of $^2H$-labeled amino acids, $^{13}C$-labeled amino acids, $^{15}N$-labeled amino acids, $^{18}O$-labeled amino acids, $^{34}S$-labeled amino acids, and $^{33}S$-labeled amino acids.

* * * * *